(12) United States Patent
Sato et al.

(10) Patent No.: US 11,350,818 B2
(45) Date of Patent: Jun. 7, 2022

(54) IN-VIVO CAMERA DEVICE AND IN-VIVO MONITORING CAMERA SYSTEM

(71) Applicant: SHARP KABUSHIKI KAISHA, Sakai (JP)

(72) Inventors: Tadahiko Sato, Sakai (JP); Hitoshi Aoki, Sakai (JP); Narakazu Shimomura, Sakai (JP); Kei Urakawa, Sakai (JP); Yan Qian, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 199 days.

(21) Appl. No.: 16/627,089

(22) PCT Filed: Jul. 2, 2018

(86) PCT No.: PCT/JP2018/025098
§ 371 (c)(1),
(2) Date: Dec. 27, 2019

(87) PCT Pub. No.: WO2019/009256
PCT Pub. Date: Jan. 10, 2019

(65) Prior Publication Data
US 2020/0138280 A1 May 7, 2020

(30) Foreign Application Priority Data
Jul. 4, 2017 (JP) .............................. JP2017-130802

(51) Int. Cl.
*A61B 1/05* (2006.01)
*A61B 1/00* (2006.01)
*A61B 1/045* (2006.01)

(52) U.S. Cl.
CPC ............ *A61B 1/05* (2013.01); *A61B 1/00018* (2013.01); *A61B 1/00045* (2013.01);
(Continued)

(58) Field of Classification Search
CPC ... A61B 1/05; A61B 1/00018; A61B 1/00045; A61B 1/00114; A61B 1/00119;
(Continued)

(56) References Cited

U.S. PATENT DOCUMENTS

| 2012/0050511 A1* | 3/2012 | Takahashi | A61B 1/041 |
| | | | 348/E7.085 |
| 2016/0143510 A1* | 5/2016 | Gotoh | A61B 1/005 |
| | | | 600/110 |
| 2018/0132707 A1 | 5/2018 | Aoki et al. | |

FOREIGN PATENT DOCUMENTS

WO 2016/203864 A1 12/2016

* cited by examiner

*Primary Examiner* — Michael J Carey
*Assistant Examiner* — Christen A. Sharpless
(74) *Attorney, Agent, or Firm* — ScienBiziP, P.C.

(57) ABSTRACT

An in-vivo camera device and an in-vivo monitoring camera system more excellent in usability are proposed. An in-vivo camera device includes a camera unit introduced into a body, a support member, and a camera-side cable. The support member has a trocar connection portion for connection with a trocar at a front end side, and is connected to the trocar in a state in which the trocar connection portion is fitted into the trocar by applying tensile force to the camera-side cable passing through the trocar. The support member is provided with a guide introduction portion that is formed to be relatively long at the front end side as a stabilization structure for stabilizing connection with the trocar.

6 Claims, 33 Drawing Sheets

(52) U.S. Cl.
CPC ...... *A61B 1/00114* (2013.01); *A61B 1/00119* (2013.01); *A61B 1/00124* (2013.01); *A61B 1/00154* (2013.01); *A61B 1/045* (2013.01)

(58) Field of Classification Search
CPC . A61B 1/00124; A61B 1/00154; A61B 1/045; A61B 1/00149; A61B 1/3132; A61B 1/0684; A61B 1/053; A61B 1/0676; H04N 7/18
USPC .......................................................... 600/160
See application file for complete search history.

11: CAMERA UNIT
12: CAMERA-SIDE CABLE
13: SUPPORT MEMBER
32a to 32c: TROCAR
33a, 33c: FORCEPS
34: ENDOSCOPE
31: TROCAR
15a: CAMERA-SIDE CABLE CONNECTOR
15b: APPARATUS-SIDE CABLE CONNECTOR
16: APPARATUS-SIDE CABLE
17: CAMERA UNIT CONTROL APPARATUS
18: DISPLAY
117: CAMERA UNIT CONTROL APPARATUS
118: DISPLAY
41: ABDOMINAL WALL
42: ORGAN

FIG. 6
(a)
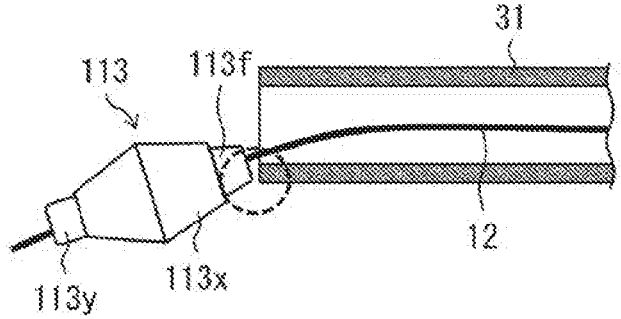
(b)
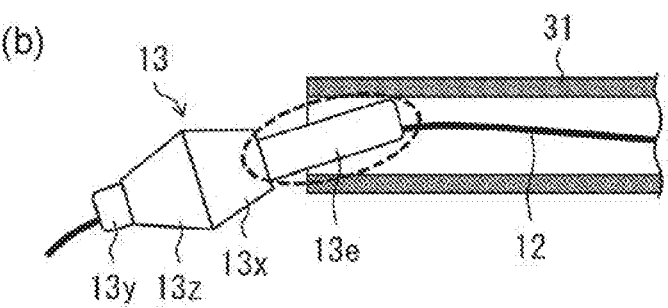
12: CAMERA-SIDE CABLE
13: SUPPORT MEMBER
13e: GUIDE INTRODUCTION PORTION
13x: TROCAR CONNECTION PORTION
13y: PROTRUSION TYPE JOINT PORTION
13z: ROOT PORTION
31: TROCAR
113: SUPPORT MEMBER OF RELATED ART
113f: GUIDE INTRODUCTION PORTION
113x: TROCAR CONNECTION PORTION
113y: PROTRUSION TYPE JOINT PORTION FIG. 9
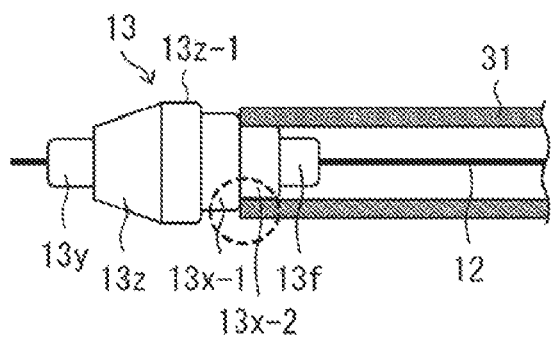
(a)
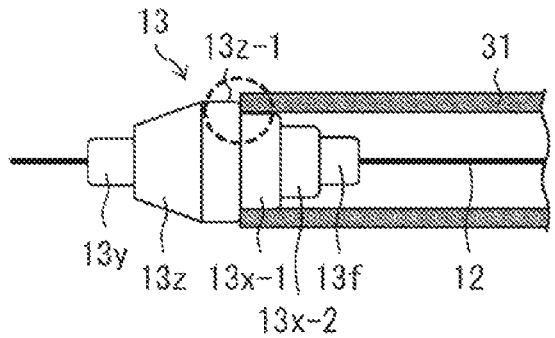
(b)
12: CAMERA-SIDE CABLE
13: SUPPORT MEMBER
13f: INTRODUCTION PORTION
13x-1: LARGE-DIAMETER TROCAR CONNECTION PART
13x-2: SMALL-DIAMETER TROCAR CONNECTION PART
13y: PROTRUSION TYPE JOINT PORTION
13z: ROOT PORTION
13z-1: COLUMNAR PART
31: TROCAR FIG. 12
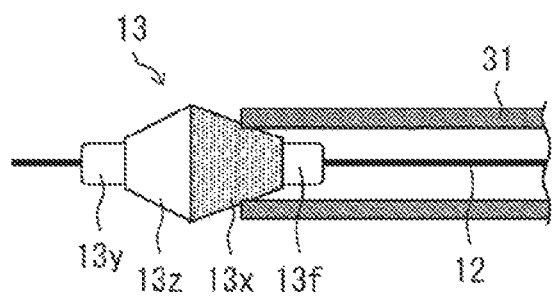
(a)
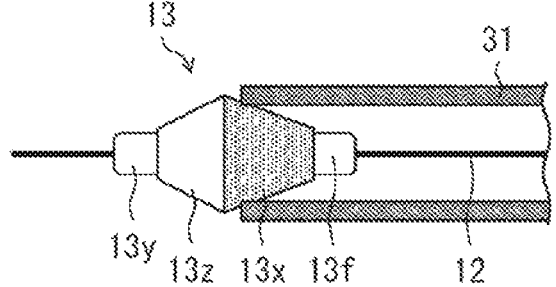
(b)
12: CAMERA-SIDE CABLE
13: SUPPORT MEMBER
13f: INTRODUCTION PORTION
13x: TROCAR CONNECTION PORTION
13y: PROTRUSION TYPE JOINT PORTION
13z: ROOT PORTION
31: TROCAR

FIG. 13
(a)
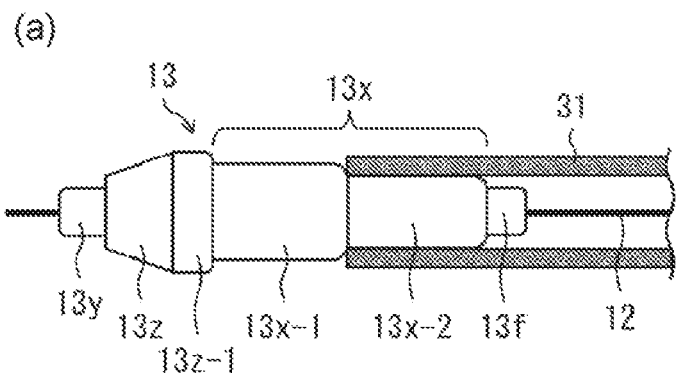
(b)
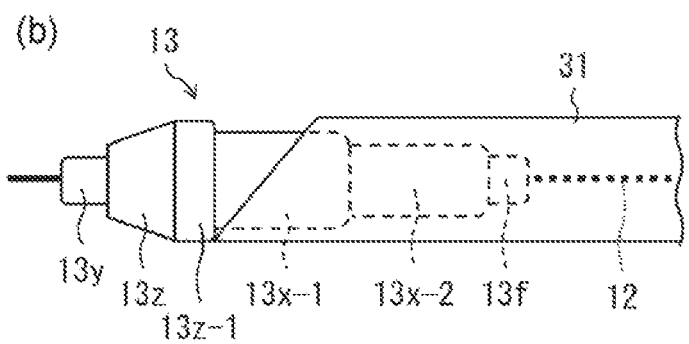
12: CAMERA-SIDE CABLE
13: SUPPORT MEMBER
13f: INTRODUCTION PORTION
13x: TROCAR CONNECTION PORTION
13x-1: LARGE-DIAMETER TROCAR CONNECTION PART
13x-2: SMALL-DIAMETER TROCAR CONNECTION PART
13y: PROTRUSION TYPE JOINT PORTION
13z: ROOT PORTION
13z-1: COLUMNAR PART
31: TROCAR

FIG. 14

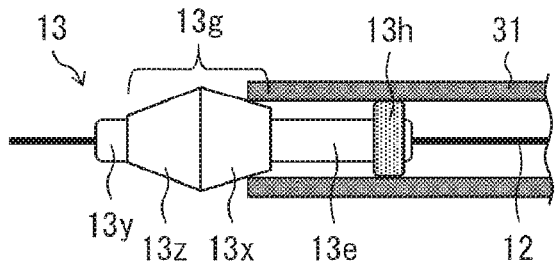

12: CAMERA-SIDE CABLE
13: SUPPORT MEMBER
13e: GUIDE INTRODUCTION PORTION
13g: MAIN BODY SECTION
13h: ELASTIC MEMBER
13x: TROCAR CONNECTION PORTION
13y: PROTRUSION TYPE JOINT PORTION
13z: ROOT PORTION
31: TROCAR

FIG. 15

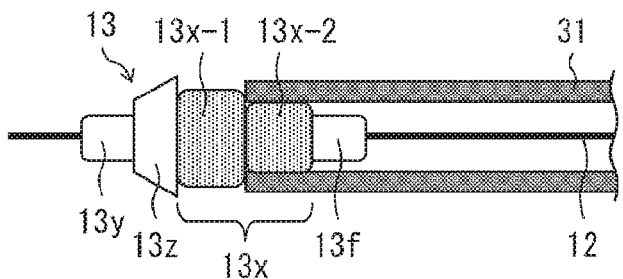

12: CAMERA-SIDE CABLE
13: SUPPORT MEMBER
13f: INTRODUCTION PORTION
13x: TROCAR CONNECTION PORTION
13x-1: LARGE-DIAMETER TROCAR CONNECTION PART
13x-2: SMALL-DIAMETER TROCAR CONNECTION PART
13y: PROTRUSION TYPE JOINT PORTION
13z: ROOT PORTION
31: TROCAR

IN-VIVO CAMERA DEVICE AND IN-VIVO MONITORING CAMERA SYSTEM

TECHNICAL FIELD

The present invention relates to an in-vivo camera device provided with an imaging unit that is introducible into the body, and an in-vivo monitoring camera system.

BACKGROUND ART

An endoscopic operation is a minimally invasive operation of performing examination or therapeutic treatment without subjecting a patient to abdominal surgery. In the endoscopic operation, a treatment tool such as forceps and an endoscope are separately introduced into a body cavity of a patient, and an operator captures an image at a front end of the treatment tool inserted into the body cavity within an observation visual field of the endoscope, and performs treatment work while observing a state of treatment using the treatment tool for an affected part with the endoscope. In the endoscopic operation, the treatment tool and the endoscope are introduced into the body cavity through a tubular instrument (a so-called trocar) that punctures a body wall (for example, an abdominal wall) of the abdomen of the patient.

The operator makes the endoscope come close to an organ, enlarges an image thereof, and performs incision or suturing, but, in this case, a visual field of the operator is considerably narrowed. Thus, there is the need for a device that enables wide recognition of states in a non-work region (for example, motion of the treatment tool, a bleeding state, and a remaining state of a residue such as a gauze in the non-work region).

The applicant of the present specification has invented the in-vivo monitoring camera system disclosed in PTL 1 as a device coping with such need. In the system, an imaging unit is fixed to a position, where the inside of the body can be observed in a bird's eye view, inside the body by using a support member (support tube). The support member has a connection portion with a trocar on one end side, and has a joint portion with the imaging unit on the other end side, and a cable of the imaging unit is inserted into the inside thereof. The cable of the imaging unit inserted into the inside of the support member is pulled toward the outer side of the body through the tubular instrument, and thus the support member is connected to an end (an end on the inner side of the body) of the tubular instrument in a state in which the connection portion is fitted thereinto.

CITATION LIST

Patent Literature

PTL 1: International Publication No. 2016/203864

SUMMARY OF INVENTION

Technical Problem

In the in-vivo monitoring camera system disclosed in PTL 1, it is possible to achieve effects that a connection defect of the cable is less likely to occur by increasing support force for the imaging unit such that reliability is improved, and an operator can change a direction of the imaging unit inside of the body by operating the trocar such that usability is improved. However, there is room for further improvement.

An aspect of the present invention is directed to providing an in-vivo camera device and an in-vivo monitoring camera system more excellent in usability.

Solution to Problem

In order to solve the problem, an in-vivo camera device according to an aspect of the present invention includes an imaging unit that is introduced into the body; a support member that has a connection portion with a tubular instrument, of which one end is introduced into a body, at a front end side and has a joint portion with the imaging unit at a rear end side; and a cable that is connected to the imaging unit and passes through the support member, in which the connection portion is formed such that a front end side is formed thinner than a rear end side, the support member is connected to the tubular instrument in a state in a state in which the connection portion is fitted into the tubular instrument, and the support member has a stabilization structure for stabilizing connection with the tubular instrument.

In order to solve the problem, an in-vivo monitoring camera system according to another aspect of the present invention includes the in-vivo camera device according; and a control system that includes at least a display device.

Advantageous Effects of Invention

According to an aspect of the present invention, an effect is achieved in which it is possible to provide an in-vivo camera device and an in-vivo monitoring camera system more excellent in usability through stabilization of connection between a tubular instrument and a support member.

BRIEF DESCRIPTION OF DRAWINGS

FIG. 2 illustrates a configuration of a camera unit of the in-vivo camera device, in which FIG. 2(a) is a sectional view thereof, and FIG. 2(b) is a top view thereof.

FIG. 6 is a partially sectional schematic view for describing an effect achieved by forming an introduction portion of the support member illustrated in FIG. 5 to be long, in which FIG. 6(a) illustrates the related art in which an introduction portion is short, and FIG. 6(b) illustrates the support member having a long introduction portion of the present embodiment.

FIG. 7 is a partially sectional schematic view for describing another effect achieved by forming an introduction portion of the support member illustrated in FIG. 5 to be long, in which FIG. 7(a) illustrates the related art in which an introduction portion is short, and FIG. 7(b) illustrates the support member having a long introduction portion of the present embodiment.

FIG. 9 is a partially sectional schematic view for describing an effect achieved by a stepped trocar connection portion of the support member illustrated in FIG. 8, in which FIG. 9(a) illustrates a state in which the support member is attached to a thin trocar, and FIG. 9(b) illustrates a state in which the support member is attached to a thick trocar.

FIG. 12 is a partially sectional schematic view for describing an effect achieved by a trocar connection portion, formed of an elastic body, of the support member illustrated in FIG. 10, in which FIG. 12(a) illustrates a state in which the support member is attached to a thin trocar, and FIG. 12(b) illustrates a state in which the support member is attached to a thick trocar.

FIG. 13 illustrates still another embodiment of the present invention, and is a schematic view for describing a configuration of a support member of an in-vivo camera device and an effect achieved by the configuration, in which FIG. 13(a) illustrates a state in which the support member is attached to a thin trocar, and FIG. 13(b) illustrates a state in which the support member is attached to a thick trocar having a front end obliquely cut shape.

FIG. 14 illustrates still another embodiment of the present invention, and is a partially sectional schematic view for describing a configuration of a support member and an effect achieved by the configuration.

FIG. 15 illustrates still another embodiment of the present invention, and is a partially sectional schematic view for describing a configuration of a support member and an effect achieved by the configuration.

FIG. 16 illustrates still another embodiment of the present invention, in which FIG. 16(a) is a front view illustrating a configuration of a support member, and FIG. 16(b) is a sectional view illustrating main portions of the support member.

DESCRIPTION OF EMBODIMENTS

Embodiment 1

Figure 1:
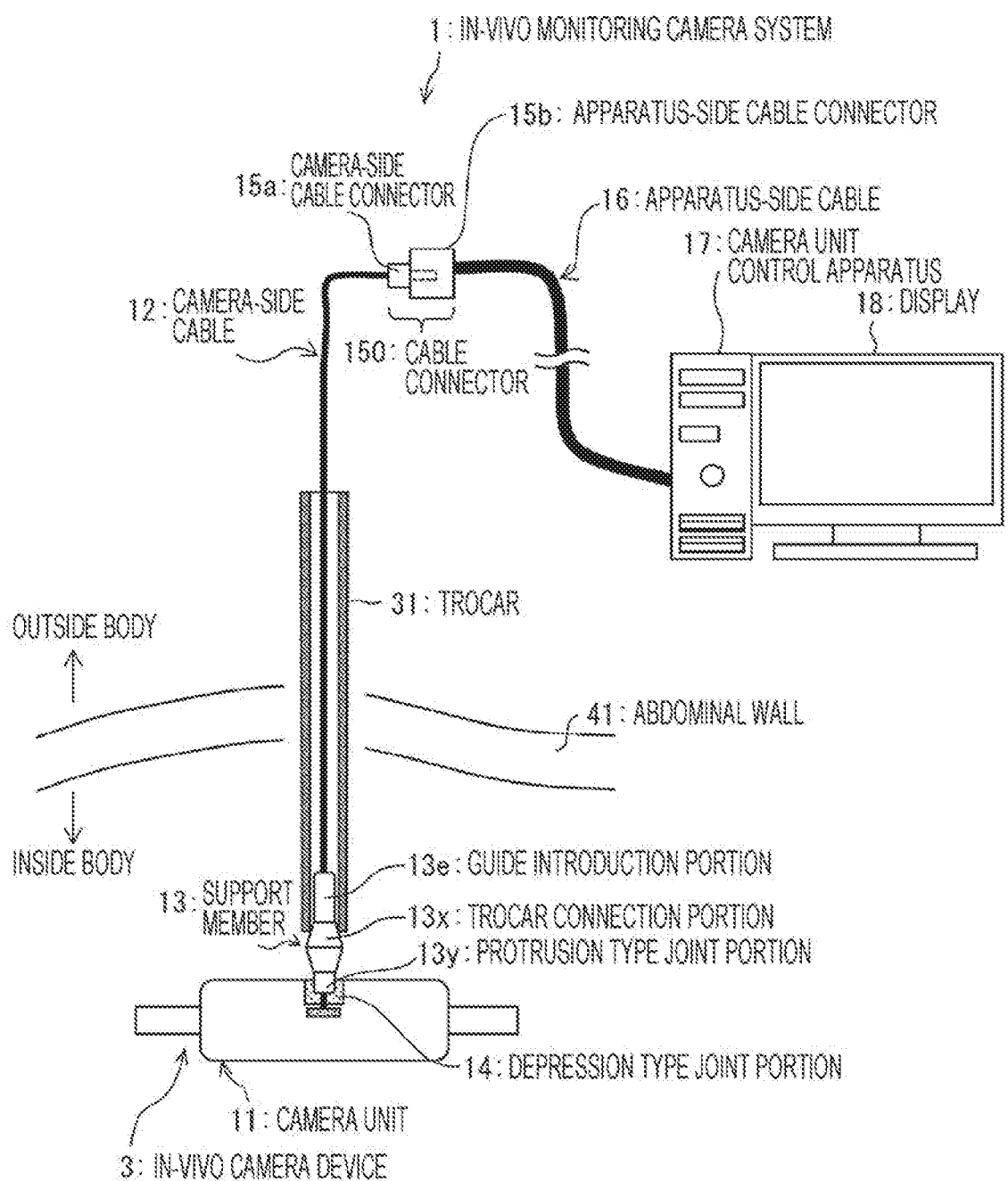
FIG. 1 illustrates an embodiment of the present invention, and is a schematic diagram illustrating a configuration of an in-vivo monitoring camera system including an in-vivo camera device.

With reference to FIGS. 1 to 7, embodiments of the present invention will be described as follows. A shape and dimensions such as a length, a size, and a width of a constituent element illustrated in each drawing do not reflect an actual shape or actual dimensions therein, and are changed as appropriate for clarification and simplification of the drawing.

(Configuration of In-Vivo Monitoring Camera System 1)

FIG. 1 is a schematic diagram illustrating a configuration of an in-vivo monitoring camera system 1 related to an aspect of the present invention. As illustrated, the in-vivo monitoring camera system 1 includes an in-vivo camera device 3 provided with a camera-side cable 12, and a camera unit 11 (imaging unit) and a support member 13 introduced into the body; a control system; and an apparatus-side cable 16 connecting the camera-side cable 12 and the control system to each other. The control system includes a camera unit control apparatus 17 and a display 18 (display device), and one end of the apparatus-side cable 16 is connected to the camera unit control apparatus 17. The in-vivo camera device 3 includes the camera unit 11, the support member 13, the camera-side cable 12, and a camera-side cable connector 15a which will be described later.

The camera-side cable 12 has the protrusion type camera-side cable connector 15a on an opposite side to a connection end with the camera unit 11. The apparatus-side cable 16 has a depression type apparatus-side cable connector 15b on an opposite side to a connection end with the camera unit control apparatus 17. An operator fits the camera-side cable connector 15a and the apparatus-side cable connector 15b to each other, and thus connects the camera-side cable 12 to the apparatus-side cable 16. A depression type camera-side cable connector and a protrusion type apparatus-side cable connector may be fitted to each other. FIG. 1 illustrates a single pin of the camera-side cable connector 15a, but, typically, the number of pins corresponds to the number of electric wires used in a cable.

The camera-side cable 12 and the apparatus-side cable 16 are connected to each other, and thus the camera unit 11 and the camera unit control apparatus 17 are electrically connected to each other. Consequently, an image captured by the camera unit 11 is transmitted to the camera unit control apparatus 17. The camera unit control apparatus 17 displays the image transmitted from the camera unit 11 on the display 18, and transmits a control signal to the camera unit 11. The camera unit control apparatus 17 and the display 18 may be integrally provided, and may be separately provided.

The camera-side cable connector 15a is drawn to the outside of the body through a trocar 31. Thus, an outer diameter of the camera-side cable connector 15a is smaller than at least an inner diameter of the trocar 31. In other words, in a case where the outer diameter of the camera-side cable connector 15a is made small, the inner diameter of the trocar 31 can be made small, and a diameter of the support member 13 can be made small. Consequently, the in-vivo monitoring camera system 1 achieves an effect of improving minimal invasiveness.

The camera-side cable 12 and the camera-side cable connector 15a are temporarily returned to the inside of the body when the camera unit 11 is recovered. Thus, the apparatus-side cable connector 15b and a portion with a predetermined length of the apparatus-side cable 16 coming into contact with the camera-side cable 12 are required to be kept clean.

As illustrated, the in-vivo monitoring camera system 1 employs a wired method in transmission of signals between the camera unit 11 and the camera unit control apparatus 17. Consequently, a transmission rate can be increased, and signals can be stably transmitted and received. Communication can be performed at lower power than in a wireless method, and the camera unit 11 can be miniaturized as a result of being supplied with power from the outside. Therefore, an injury when the camera unit 11 is introduced into the body can be reduced due to the miniaturization. Consequently, an effect of improving minimal invasiveness is improved.

In the in-vivo monitoring camera system 1, an end of the trocar 31, on the inner side of the body, puncturing an abdominal wall 41 is connected to the support member 13 via a trocar connection portion 13x of the support member 13. The camera unit 11 introduced into the body is joined to the support member 13 via a protrusion type joint portion 13y of the support member 13. Details of the support member 13 will be described later. In the present embodiment, as illustrated, a body wall will be described as the abdominal wall 41, but a body wall is not limited to the abdominal wall 41.

(Configuration of Camera Unit 11)

Figure 2:
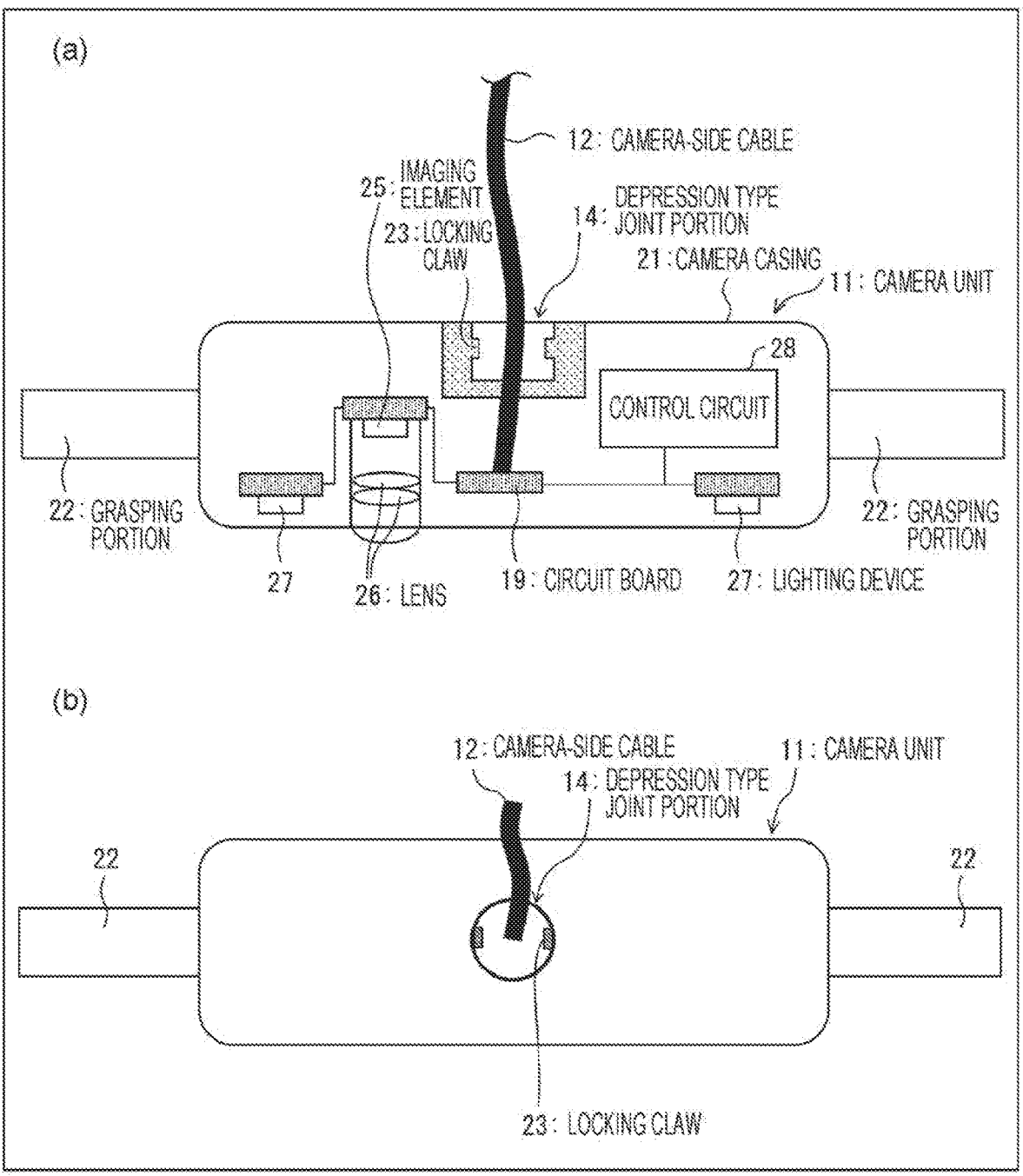

FIG. 2 illustrates a configuration of the camera unit 11 of the in-vivo camera device 3, in which FIG. 2(a) is a sectional view, and FIG. 2(b) is a top view. As illustrated in FIGS. 2(a) and 2(b), the camera unit 11 includes a circuit board 19, an imaging element 25, a control circuit 28, and a lighting device 27 connected to the circuit board 19, and a lens 26 in a camera casing 21.

A depression type joint portion 14 is provided in an upper surface of the camera casing 21. The depression type joint portion 14 has a circular opening hole structure, and is provided with a locking claw 23 on an inner wall thereof. A grasping portion 22 is provided on each of both opposite side surfaces of the camera casing 21. An operator grips the grasping portions 22 by using forceps, and thus changes a direction of the camera unit 11 introduced into the body or moves the camera unit 11.

The camera-side cable 12 is connected to the circuit board 19, and is guided to the outside of the camera unit 11 through the depression type joint portion 14. A connection location between the circuit board 19 and the camera-side cable 12 is sealed with a resin or the like. At a location (a bottom of the depression type joint portion 14) at which the camera-side cable 12 is drawn inside the depression type joint portion 14, the camera-side cable 12 is adhered and fixed to the bottom of the depression type joint portion 14, for example, fixed thereto through sealing by using an adhesive or an O-ring, and thus there is a configuration in which permeation of water or a foreign substance from the location (to the inside of the camera unit 11) does not occur. The camera-side cable 12 is introduced into a body cavity through the trocar, and is made of a flexible material.

The imaging element 25 is a CCD or a CMOS image sensor, and the lighting device 27 clarifies an image captured by the camera unit 11 by lighting the inside of the body. The lighting device 27 preferably has a small size, and, for example, an LED may be preferably used. As illustrated in FIG. 2, a plurality of lighting devices 27 may be provided in the camera casing 21.

(Usage of In-Vivo Monitoring Camera System)

Figure 3:
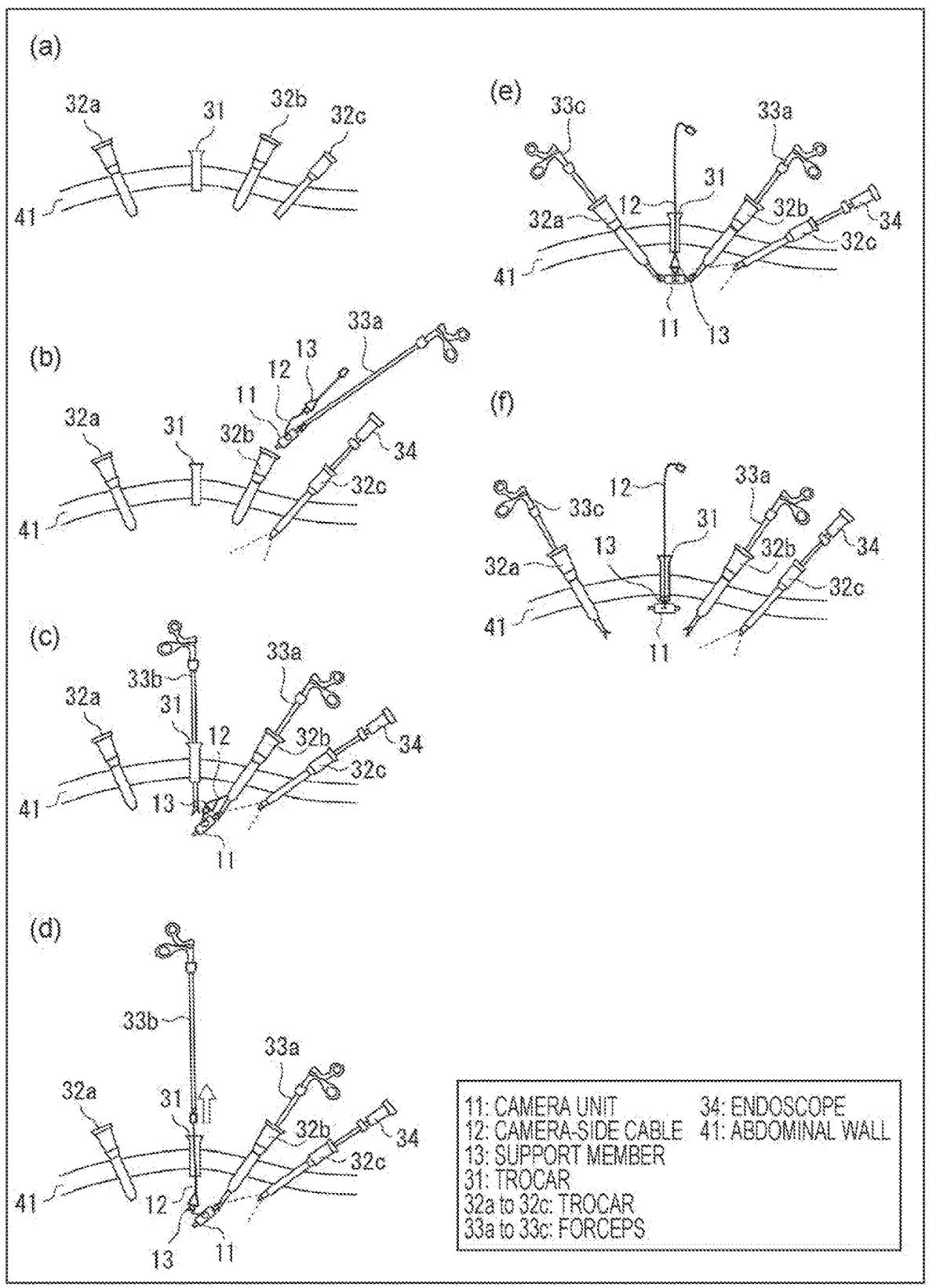
FIGS. 3(a) to 3(g) are schematic diagrams illustrating a method of installing the camera unit inside the body.
Figure 4:
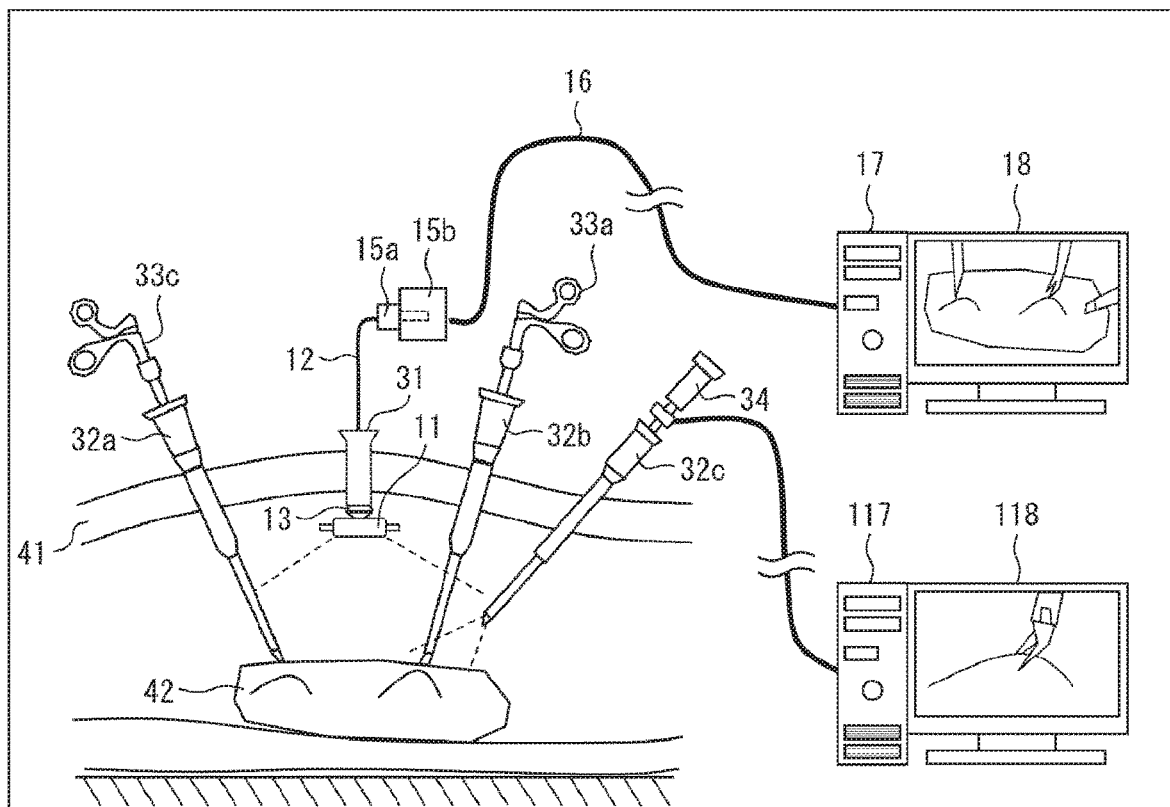
FIG. 4 is a schematic diagram illustrating a use status of the in-vivo monitoring camera system.
Figure 5:
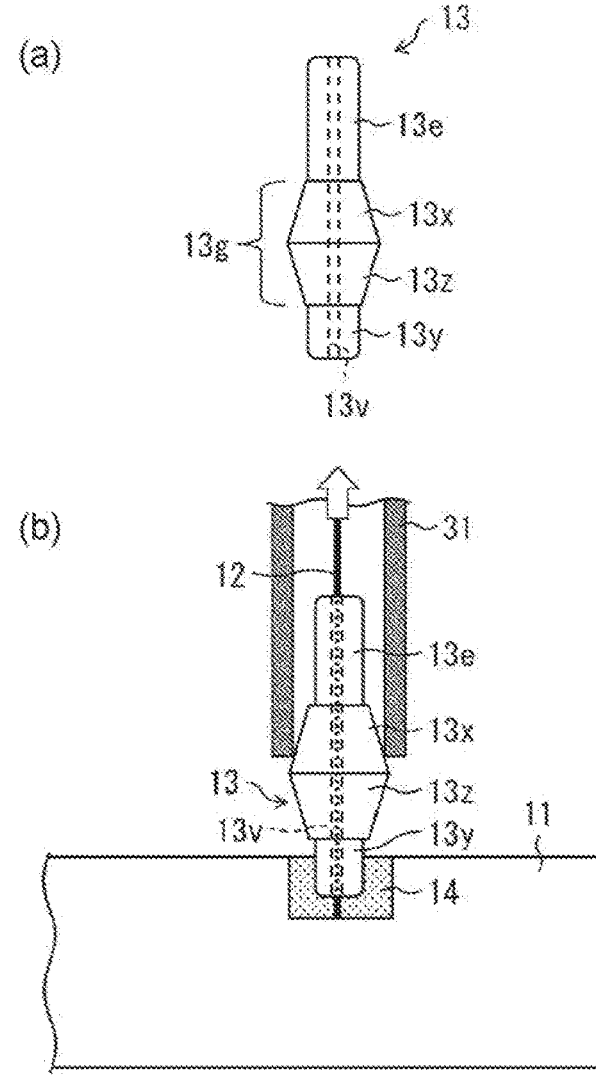
FIG. 5(a) is a front view illustrating a configuration of a support member of the in-vivo camera device.
FIG. 5(b) is a partially sectional schematic view illustrating attachment among the support member, a trocar, and the camera unit.

FIGS. 3(a) to 3(g) are schematic diagrams illustrating a method of installing the camera unit inside of the body, and FIG. 4 is a schematic diagram illustrating a use status of the in-vivo monitoring camera system.

As illustrated in FIG. 3(a), first, an operator forms holes (ports) for inserting forceps 33a to 33c and an endoscope 34 into the body cavity in the abdominal wall 41, and inserts trocars 32a to 32c into the ports. In order to install the camera unit 11 in the body cavity, a port is formed in the abdominal wall 41 at a position where the whole organ including an affected part is viewable (a position where the inside of the body is observable in a bird's eye view), and the trocar 31 is inserted into the port. Specifically, in a state in which a needle-shaped obturator passes through the trocar 31, the obturator punctures the port position, and thus the trocar 31 is inserted into the abdominal wall 41.

The trocar 31 preferably has a small diameter in order to realize minimal invasiveness. Specifically, the diameter of the trocar 31 is preferably 3 mm or less. After at least one of the trocars 32a to 32c and the trocar 31 is inserted, the operator feeds a gas to the inside of the body through the trocar, so as to expand the body cavity in advance, so that a space for inserting an instrument is secured.

Next, as illustrated in FIG. 3(b), the operator inserts the endoscope 34 into the body cavity through the trocar 32c, and inserts the camera unit 11 gripped with the forceps 33a, the camera-side cable 12, and the support member 13 through which the camera-side cable 12 passes into the body cavity through the trocar 32b while observing the inside of the body by using the endoscope 34.

Next, as illustrated in FIG. 3(c), the operator moves the camera unit 11 to the vicinity of the trocar 31 by operating the forceps 33a, and inserts the forceps 33b into the body cavity through the trocar 31.

Next, as illustrated in FIG. 3(d), the operator extracts the forceps 33b from the trocar 31 while holding the camera-side cable 12 with the forceps 33b, and thus guides the camera-side cable 12 to the outside of the body. In this case, the camera unit 11 (the grasping portion thereof) is in a state of being gripped with the forceps 33a. An example in which the camera unit 11 side is inserted into the body cavity is illustrated in the figure, but there may be procedures in which the camera-side cable connector 15a side is first inserted into the body cavity, and the camera unit 11 is inserted into the body while holding the camera-side cable connector 15a with forceps.

Next, as illustrated in FIG. 3(e), the operator pulls up the camera-side cable 12 guided to the outside of the body with the forceps or the hand, and thus causes a front end of the support member 13 to come close to an opening of the trocar 31.

Next, as illustrated in FIG. 3(f), the operator further pulls up the camera-side cable 12 and the camera unit 11 so as to insert one end (trocar connection portion) of the support member 13 into an end of the trocar 31 on the inner side of the body, and fits the camera unit 11 into the other end (protrusion type joint portion) thereof so as to connect one end (trocar connection portion) of the support member 13 to the end of the trocar 31 on the inner side of the body and also to join the other end (protrusion type joint portion) to the camera unit 11. The camera-side cable 12 is stopped at the abdominal wall 41 or the like such that the tension of the camera-side cable 12 pulling up the camera unit 11 is maintained.

After the camera unit 11 is installed inside the body, as illustrated in FIG. 4, the camera-side cable connector 15a is fitted into the apparatus-side cable connector 15b, and thus the camera-side cable 12 and the apparatus-side cable 16 are connected to each other. Consequently, a local image of a treatment part is displayed on a display 118 by an endoscope control apparatus 117, and an image of the whole organ 42 captured by the camera unit 11 is displayed on the display 18 by the camera unit control apparatus 17.

After-use of the in-vivo monitoring camera system is as follows. First, the operator inserts the forceps 33c into a gap between the support member 13 and the camera unit 11 in a state in which the grasping portion 22 of the camera unit 11 inside of the body is gripped with the forceps 33a, and separates the support member 13 from the camera unit 11 by operating the forceps 33c. Next, the operator pulls the support member 13 away from the trocar 31, and then guides the camera unit 11, the camera-side cable 12, and the support member 13 from the trocar 32b to the outside of the body.

In the example illustrated in FIG. 3, there is a configuration in which the front end of the camera-side cable 12 is drawn to the outside of the body with the forceps 33b through the trocar 31, but a dedicated jig connectable with the camera-side cable connector 15a may be used to pull up the camera-side cable 12. For example, there may be a configuration in which a magnet or a magnetic body is attached to the front end of the camera-side cable connector 15a, a pull-up tool (not illustrated) having a holding magnet at a front end thereof is inserted into the trocar 31, and pulls out the camera-side cable connector 15a by attraction between attraction forces.

(Configuration of Support Member 13)

FIG. 5(a) is a front view illustrating a configuration of the support member 13, and FIG. 5(b) is a partially sectional schematic view illustrating attachment among the support member 13, the trocar 31, and the camera unit 11. In the present specification, for convenience of description, a side connected to the trocar 31 in the support member 13 will be referred to as a front end side, and a side connected to the camera unit 11 in the support member 13 will be referred to as a rear end side. A side inserted into the body in the trocar 31 will be referred to as a front end side.

As illustrated in FIGS. 5(a) and 5(b), the support member 13 has a spindle-shaped main body section 13g, and an upper portion of the main body section 13g corresponds to a truncated conic trocar connection portion 13x. In a case where the support member 13 is used for two types of trocars 31 with, for example, outer diameters of 5 mm and 3 mm, a diameter of a thick rear end side of the trocar connection portion 13x is set to be larger than an inner diameter of the thick trocar 31 of 5 mm. A diameter of a thin front end side of the trocar connection portion 13x is designed to be smaller than an inner diameter of the thin trocar 31 of 3 mm. As mentioned above, the trocar connection portion 13x has a truncated conic shape, and a surface thereof butting with the trocar 31 has a tapered shape, and can thus cope with the trocars 31 with different outer diameter sizes.

A guide introduction portion 13e that is a guide portion when the front end of the support member 13 is guided to the inside of the trocar 31 is provided on the front end side of the trocar connection portion 13x. In the support member 13 of the present embodiment, the guide introduction portion 13e is formed to be relatively long in an axial direction, and this will be described later.

A lower portion of the main body section 13g corresponds to a truncated conic root portion 13z, and the columnar protrusion type joint portion 13y that is fitted to the depression type joint portion 14 (refer to FIG. 1) of the camera unit 11 is provided on the rear end side of the root portion 13z. Since the root portion 13z has a truncated conic shape thinned toward the protrusion type joint portion 13y, the tapered portion is pinched with forceps (refer to the forceps 33a and 33c in FIG. 3), and the support member 13 can be easily separated from the camera unit 11 by sliding the forceps (refer to FIGS. 10(b) and 10(c) which will be described later).

The support member 13 has a cable hole 13v that penetrates from the front end side to the rear end side and through which the camera-side cable 12 passes. A hole diameter of the cable hole 13v is preferably a size of contacting the camera-side cable 12 with some extent of load. Some extent of load is a load in which the support member 13 is held at an original position unless force is particularly applied, and is moved along the camera-side cable 12 in a case where light force is applied.

In the support member 13, the camera-side cable 12 passing through the cable hole 13v is pulled up such that the guide introduction portion 13e of the front end thereof enters the trocar 31, and thus the conic surface (tapered surface) of the trocar connection portion 13x butts with the front end (the end on the inner side of the body) of the trocar 31. The camera-side cable 12 is further pulled up in this state such that the depression type joint portion 14 of the camera unit 11 is fitted into the protrusion type joint portion 13y of the support member 13, and thus the support member 13 is joined to the camera unit 11.

Tensile force is continuously applied to the camera-side cable 12 (tension is continuously applied thereto) in this state, and thus the support member 13 is connected to the trocar 31 in a state in which the trocar connection portion 13x is fitted into the inside of the trocar 31. The camera unit 11 is attached to the rear end side of the support member 13 of which the front end side is connected to the trocar 31, and is thus fixed to the trocar 31 via the support member 13.

In the support member 13 of the present embodiment, a configuration to be focused is related to a stabilization structure for stabilizing connection between the trocar 31 and the support member 13. The support member 13 of the present embodiment has the guide introduction portion 13e that is formed to be relatively long in the axial direction as the stabilization structure. Herein, the guide introduction portion 13e is formed in a columnar shape.

FIG. 6 is a partially sectional schematic view for describing an effect achieved by forming the guide introduction portion 13e of the support member 13 to be long. FIG. 6(a) illustrates a support member of the related art having a short guide introduction portion 113f, and FIG. 6(b) illustrates the support member 13 of the present embodiment having the long guide introduction portion 13e. As illustrated in FIGS. 6(a) and 6(b), the support members 113 and 13 are used at an angle substantially close to horizontality during an actual operation.

As illustrated in FIG. 6(a), in the support member 113 of the related art, the guide introduction portion 113f is short, and thus a length of a portion thereof entering the trocar 31 is small. Thus, in a case where the camera-side cable 12 becomes loose, the support member 113 may be released from the trocar 31. In a case where the support member 113 is released from the trocar 31, the camera unit 11 (not illustrated) attached to a protrusion type joint portion 113y is turned just below by its weight, and thus a visual field direction is deviated.

In the configuration of the support member 113, in a case where the support member is temporarily released from the trocar 31, even though the camera-side cable 12 is pulled in a state in which the trocar 31 is horizontal, it is supposed that the camera-side cable is caught in the opening of the trocar 31 (in the figure, a location indicated by the dotted O) and thus cannot be easily returned to the original position.

In contrast, as illustrated in FIG. 6(b), the support member 13 of the present embodiment is provided with the long guide introduction portion 13e, and thus a length of a portion thereof entering the inside of the trocar 31 is large. Thus, even though the camera-side cable 12 becomes loose, the long guide introduction portion 13e is caught in the inner wall of the trocar 31, and is thus less likely to be released from the trocar 31 (in the figure, a location indicated by the dotted O). Even in a state in which the trocar 31 is horizontal, unless the support member 13 completely comes out of the trocar 31, the support member 13 can be easily returned to the original position by just pulling the camera-side cable 12.

Figure 7:
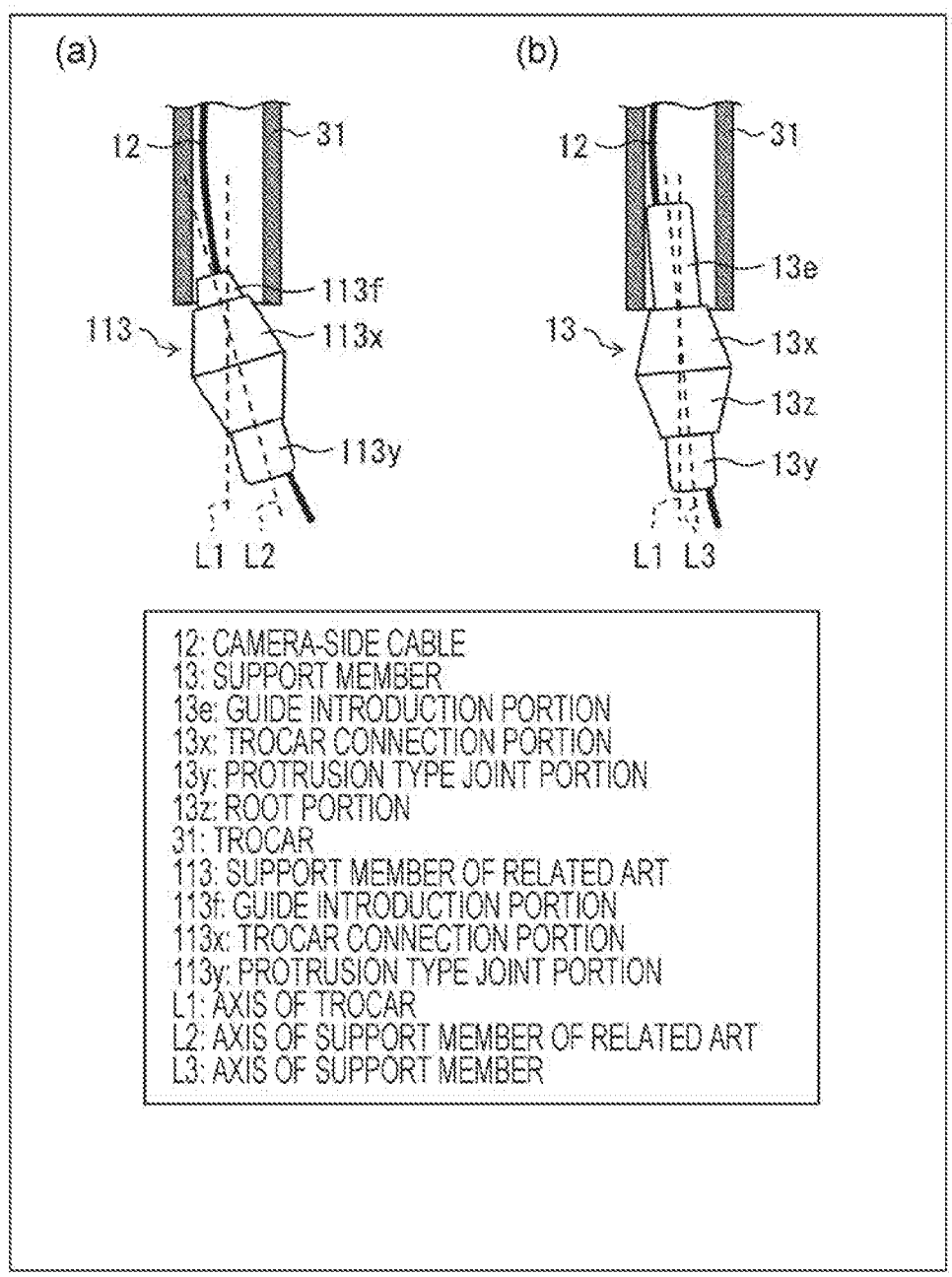

FIG. 7 is a partially sectional schematic view for describing another effect achieved by forming the guide introduction portion 13e of the support member 13 to be long. FIG. 7(a) illustrates a support member 13 of the related art having the short guide introduction portion 113f, and FIG. 7(b) illustrates the support member 13 of the present embodiment having the long guide introduction portion 13e.

As illustrated in FIG. 7(a), in the support member 113 of the related art, the guide introduction portion 113f is short, and thus a length of a portion thereof entering the trocar 31 is small. Thus, in a case where the camera-side cable 12 becomes loose, an axis L2 of the support member 113 may be greatly deviated relative to an axis L1 of the trocar 31. As the deviation increases, an angular deviation in a visual field direction increases.

In contrast, as illustrated in FIG. 7(b), the support member 13 of the present embodiment is provided with the long guide introduction portion 13e, and thus a length of a portion thereof entering the inside of the trocar 31 is large. Thus, even though the camera-side cable 12 becomes loose, the long guide introduction portion 13e is caught in the inner wall of the trocar 31, and thus deviation of the axis L3 of the support member 13 relative to the axis L1 of the trocar 31 is restricted such that an angular deviation in the visual field direction can be reduced.

For example, in a case where the support member 13 is supposed to be used for two types of trocars 31 with outer diameters of 5 mm and 3 mm, the guide introduction portion 13e preferably has a length of being less likely to be released from the trocar 31 with the large diameter of 5 mm. However, a diameter (outer diameter) of the guide introduction portion 13e is required to be smaller than an inner diameter of the trocar 31 with the small diameter of 3 mm. A large length of the guide introduction portion 13e contributes to stabilization, but handling thereof is difficult when a length of the guide introduction portion 13e is too large. Thus, when taking into consideration that there is a short trocar of 60 mm among the trocars 31 generally available in the market, a length of the guide introduction portion 13e is preferably about 3 to 20 mm. However, there is a relatively long trocar 31 of about 110 mm. Thus, in a case where such a long trocar 31 is used, a length of the guide introduction portion 13e may be larger than 20 mm.

In the support member 13 of the present embodiment, the guide introduction portion 13e has a columnar shape. Due to the shape, for example, in a case where the support member 13 is inclined, the guide introduction portion 13e can be brought into contact with the inner wall of the trocar 31 earlier than that in a configuration in which the guide introduction portion 13e has a truncated conic shape that is cut off and is thinned at the front end side. Thus, the guide introduction portion 13e is less likely to be released and an angular deviation can be reduced.

The front end may be thin in the same manner as the guide introduction portion 13e (refer to FIG. 16(a)) of the support member 13 in Embodiment 7 which will be described later. Due to the shape, the front end can be smoothly introduced into the trocar 31.

Embodiment 2

Figure 10:
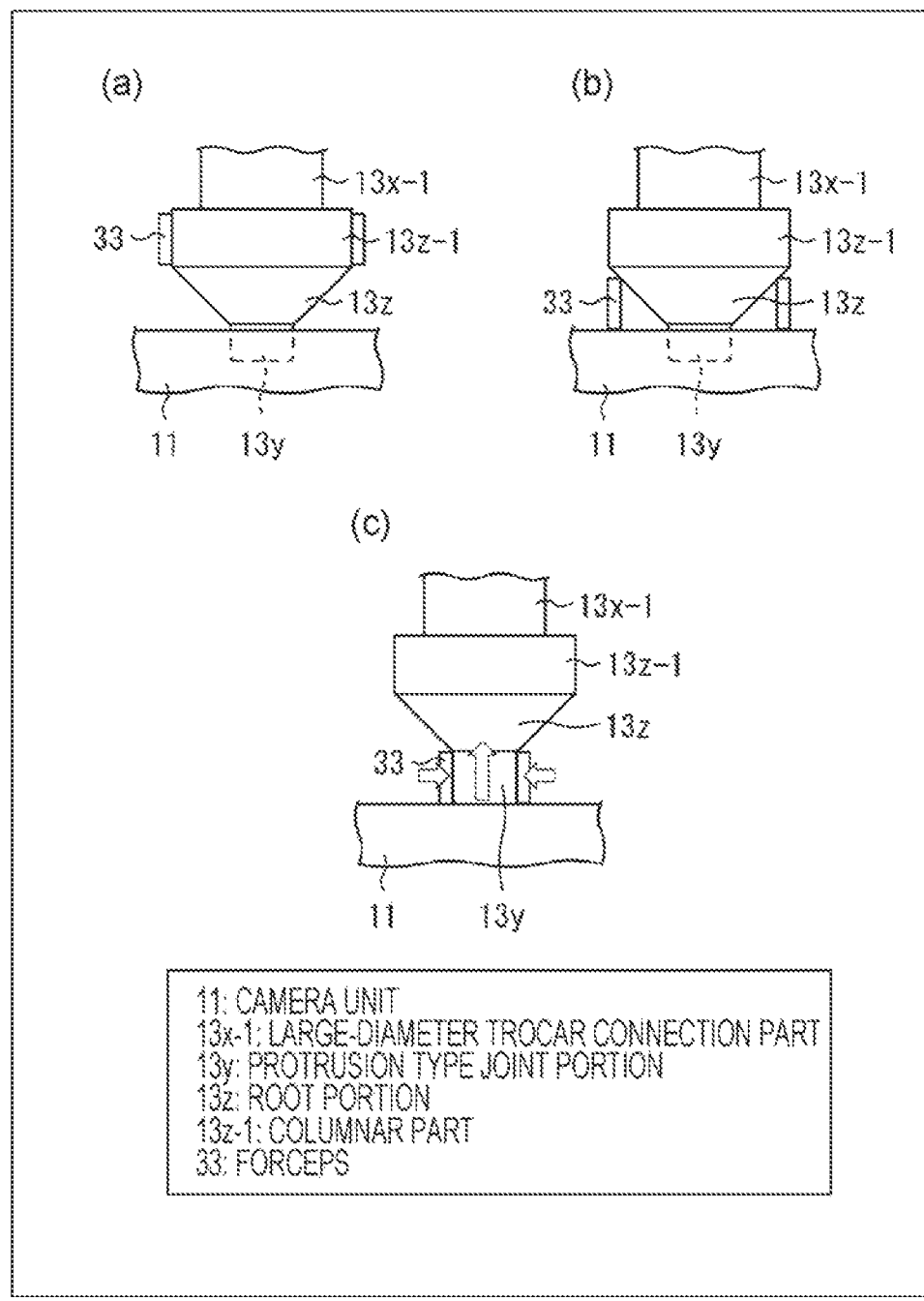
FIG. 10(a) is a diagram illustrating a method of gripping the support member.
FIGS. 10(b) and 10(c) are diagrams for describing a method of detaching a support member 13 from a camera unit 11.

Another embodiment of the present invention will be described as follows with reference to FIGS. 8 to 10. For convenience of description, a member having the same function as that of the member described in the embodiment will be given the same reference numeral, and description thereof will not be repeated.

Figure 8:
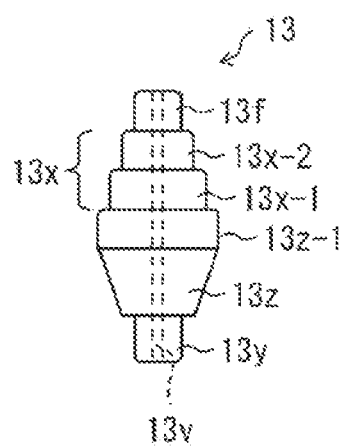
FIG. 8 illustrates another embodiment of the present invention, and is a front view illustrating a configuration of a support member of an in-vivo camera device.

FIG. 8 is a front view illustrating a configuration of a support member 13 of an in-vivo camera device 3 in the present embodiment. As illustrated in FIG. 8, the support member 13 is the same as the support member 13 of Embodiment 1 in that the root portion 13z of which the rear end side has a thin truncated conic shape is provided, and the columnar protrusion type joint portion 13y is provided on the rear end side of the root portion 13z.

A difference from the support member 13 of Embodiment 1 is that a stepped trocar connection portion 13x is provided instead of the truncated conic trocar connection portion 13x. The stepped trocar connection portion 13x is formed in a stepped shape having a plurality of columnar parts being coaxial with each other and corresponding to diameters of trocars 31 supposed to be used. In the support member 13 of the present embodiment, the trocar connection portion 13x formed in a stepped shape corresponds to a stabilization structure.

The stepped trocar connection portion 13x has a trocar connection part 13x-1 on the rear end side and a trocar connection part 13x-2 on the front end side, corresponding to a plurality of columnar parts being coaxial with each other. The trocar connection part 13x-1 on the rear end side is formed to have a diameter larger than that of the trocar connection part 13x-2 on the front end side. Hereinafter, the trocar connection part 13x-1 will be referred to as a large-diameter trocar connection part, and the trocar connection part 13x-2 will be referred to as a small-diameter trocar connection part.

In a case where the support member 13 is used for two types of trocars 31 with, for example, outer diameters of 5 mm and 3 mm, a diameter of the large-diameter trocar connection part 13x-1 is set in accordance with an inner diameter of the trocar 31 with the large diameter of 5 mm, and a diameter of the small-diameter trocar connection part 13x-2 is set in accordance with an inner diameter of the trocar 31 with the small diameter of 3 mm.

A guide introduction portion 13f at the front end may be smaller than an inner diameter of the trocar 31 with the small diameter of 3 mm, and may be formed at, for example, below 2 mm that is substantially the same as a cable diameter of the camera-side cable 12. In FIG. 8, the trocar connection portion 13x has two types such as small-diameter and large-diameter connection parts, but the number of steps of the stepped trocar connection portions may be increased to cope with more types of trocars. This is also the same for the following embodiments.

In the support member 13 of the present embodiment, a columnar part 13z-1 having a columnar shape is provided on the front end side (trocar connection portion 13x side) of the truncated conic root portion 13z. Consequently, the camera unit 11 is more easily detached from the support member 13. This will be described later.

FIG. 9 is a partially sectional schematic view for describing an effect achieved by the stepped trocar connection portion 13x of the support member 13. FIG. 9(a) illustrates a state in which the support member 13 is attached to the thin trocar 31, and FIG. 9(b) illustrates a state in which the support member 13 is attached to the thick trocar 31.

As illustrated in FIG. 9(a), the thin trocar 31 is connected by using the small-diameter trocar connection part 13x-2 on the front end side. The guide introduction portion 13f enters the inside of the thin trocar 31, and thus the small-diameter trocar connection part 13x-2 is fitted thereinto. A front end of the thin trocar 31 comes into contact with a step difference surface caused by a step difference between the small-diameter trocar connection part 13x-2 and the large-diameter trocar connection part 13x-1 (in the figure, a location indicated by the dotted O). Here, the step difference surface corresponding to an end surface of the large-diameter trocar connection part 13x-1 on the front end side functions as a stopper coming into contact with the end of the thin trocar 31.

As illustrated in FIG. 9(b), the thick trocar 31 is connected by using the large-diameter trocar connection part 13x-1 on the rear end side. The guide introduction portion 13f and the small-diameter trocar connection part 13x-2 enter the inside of the thick trocar 31, and thus the large-diameter trocar connection part 13x-1 is fitted thereinto. A front end of the thick trocar 31 comes into contact with a step difference surface caused by a step difference between the large-diameter trocar connection part 13x-1 and the columnar part 13z-1 (in the figure, a location indicated by the dotted O). Here, the step difference surface corresponding to an end surface of the columnar part 13z-1 on the front end side functions as a stopper coming into contact with the end of the thick trocar 31.

As illustrated in FIGS. 9(a) and 9(b), the small-diameter trocar connection part 13x-2 and the large-diameter trocar connection part 13x-1 have a columnar shape, and thus contact with the inner wall of the trocar 31 is surface contact. Consequently, the support member 13 is supported by the trocar 31 at the surface, and thus fixation strength (attachment strength) of the support member 13 for the trocar 31 can be increased more than in a configuration of being supported at a line in the related art. The fixation strength can be further increased by increasing an area of surface contact.

The fixation strength is increased, and thus release from the trocar 31 is less likely to occur. Since the contact with the inner wall of the trocar 31 is surface contact, it is possible to substantially reliably prevent the support member 13 from being inclined with respect to the trocar 31.

In the configuration illustrated in FIG. 8, the configuration including the short conic guide introduction portion 13f has been exemplified, but, instead of the guide introduction portion 13f, a configuration including the long guide introduction portion 13e provided in the support member 13 of Embodiment 1 may be used.

In the present embodiment, the stepped trocar connection portion 13x has two steps such as the small-diameter trocar connection part 13x-2 and the large-diameter trocar connection part 13x-1. However, the stepped trocar connection portion 13x is not limited to two steps, and may have three steps assuming that the support member is used for three or more trocars 31 having different diameters.

This is also the same for the following embodiments in which the stepped trocar connection portion 13x is provided.

FIG. 10(a) is a diagram illustrating a method of gripping the support member 13, and FIGS. 10(b) and 10(c) are diagrams for describing a method of detaching the support member 13 from the camera unit 11. In the support member 13 of the present embodiment, the truncated conic root portion 13z is provided with the columnar part 13z-1. Consequently, as illustrated in FIG. 10(a), the support member 13 can be released from the trocar 31 while the columnar part 13z-1 is pinched with the forceps 33. As illustrated in FIGS. 10(b) and 10(c), the tapered part of the root portion 13z is pinched with the forceps 33 and is slid to be raised and pulled away from the camera unit 11, and thus the support member 13 and the camera unit 11 can be easily separated from each other.

Embodiment 3

Still another embodiment of the present invention will be described as follows with reference to FIGS. 11 and 12. For convenience of description, a member having the same function as that of the member described in the embodiments will be given the same reference numeral, and description thereof will not be repeated.

Figure 11:
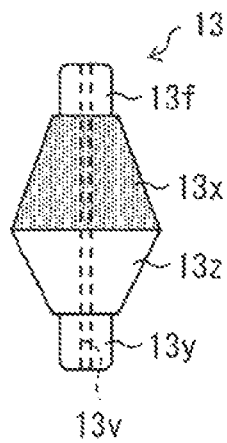
FIG. 11 illustrates still another embodiment of the present invention, and is a front view illustrating a configuration of a support member of an in-vivo camera device.

FIG. 11 is a front view illustrating a configuration of a support member 13 in the present embodiment. As illustrated in FIG. 11, in the support member 13 of the present embodiment, the trocar connection portion 13x of which the front end side has a truncated conic shape is formed of an elastic body. The elastic body is, for example, a rubber or a foam body, and an elastomer may be used. This is different from the support member 13 of Embodiment 1. In the support member 13 of the present embodiment, the trocar connection portion 13x formed of the elastic body corresponds to a stabilization structure.

FIG. 12 is a partially sectional schematic view for describing an effect achieved by the trocar connection portion 13x formed of the elastic body. FIG. 12(a) illustrates a state in which the support member 13 is attached to the thin trocar 31, and FIG. 12(b) illustrates a state in which the support member 13 is attached to the thick trocar 31.

As illustrated in FIG. 12(a), the thin trocar 31 is connected to the front end side of the trocar connection portion 13x, and, as illustrated in FIG. 12(b), the thick trocar 31 is connected to the rear end side of the trocar connection portion 13x. The trocar connection portion 13x has a truncated conic shape in which the front end side thereof is thinned, and can thus cope with trocars 31 having different outer diameter sizes.

As illustrated in FIGS. 12(a) and 12(b), the trocar connection portion 13x formed of the elastic body is fitted into the trocar 31 by strongly pulling the camera-side cable 12. In this case, the trocar connection portion 13x is more strongly fixed by elastic force (restoring force) of the elastic body and friction force of the contact surfaces than in a configuration in which the trocar connection portion is formed of a nonelastic body. Consequently, it is possible to increase fixation strength (attachment strength) between the trocar 31 and the support member 13. Since the trocar connection portion 13x is formed of the elastic body having a truncated conic shape, an inner diameter difference for each manufacturer of the trocar 31 can be absorbed, and the support member 13 can be necessarily brought into surface contact with the inner wall of the trocar 31.

In the support member 13 of the present embodiment, the root portion 13z and the protrusion type joint portion 13y are made of hard materials. This is because, in a case where the root portion 13z is formed of an elastic body, sliding of forceps on the root portion 13z deteriorates, and thus the workability for detachment of the camera unit 11 using the tapered shape of the root portion 13z deteriorates. Although not illustrated, the guide introduction portion 13f does not influence the workability of detachment, and may thus be formed of an elastic body. This is also the same for the following Examples and combined Examples.

However, in the support member 13 of the present embodiment, it is difficult to obtain the feeling of contact between the trocar 31 and the support member 13, and thus the camera-side cable 12 may be pulled strongly more than necessary. As fixation strength is increased by using an elastic body in the trocar connection portion 13x, force required to release the support member 13 from the trocar 31 is also increased. Thus, in the camera-side cable 12 and the camera unit 11 used in combination with the support member 13 of the present embodiment, cable strength and/or strength of the cable connection portion are (is) required to be more than force required to extract the support member 13 (use of an elastic body) from the trocar 31.

For example, in a case where the camera unit 11 is detached from the support member 13, and then the camera unit 11 is recovered in this state without releasing fixation between the support member 13 and the trocar 31, the camera-side cable connector 15a cannot pass through the cable hole 13v and is caught in the guide introduction portion 13e. In a case where connection strength between the camera-side cable 12 and the camera-side cable connector 15a is not sufficient, the camera-side cable is pulled more strongly in this state, the camera-side cable 12 is damaged. Conversely, in a case where the connection strength is sufficient, the camera-side cable is only pulled, and thus the fixation between the support member 13 and the trocar 31 may be released.

In the support member 13 of the present embodiment, since the support member 13 is strongly fixed to the trocar 31, the grasping portion or the like of the camera unit 11 is brought into contact with or pushed by forceps to be rotated, and thus it is possible to easily adjust a visual field direction.

Embodiment 4

Still another embodiment of the present invention will be described as follows with reference to FIG. 13. For convenience of description, a member having the same function as that of the member described in the embodiments will be given the same reference numeral, and description thereof will not be repeated.

FIG. 13 is a schematic diagram illustrating a configuration of a support member 13 in the present embodiment and an effect achieved by the configuration. FIG. 13(a) illustrates a state in which the support member 13 is attached to the thin trocar 31, and FIG. 13(b) illustrates a state in which the support member 13 is attached to the thick trocar 31 having a front end obliquely cut shape.

As illustrated in FIGS. 13(a) and 13(b), the support member 13 is provided with the small-diameter trocar connection part 13x-2 and the large-diameter trocar connection part 13x-1, formed to be long in the axial direction, forming the stepped trocar connection portion 13x of the support member 13 (refer to FIG. 8) of Embodiment 2.

With this configuration, as illustrated in FIG. 13(a), an area of surface contact between the support member 13 and the inner wall of the trocar 31 is increased, and thus fixation strength can be further increased. Consequently, it is possible to effectively prevent release from the trocar 31 or an angular deviation of the support member 13.

As illustrated in FIG. 13(b), a length of the large-diameter trocar connection part 13x-1 is made larger than a length of an obliquely cut portion of the thick trocar 31 having a front end obliquely cut shape, and thus connection therebetween may be performed. This is also the same for the small-diameter trocar connection part 13x-2.

Embodiment 5

Still another embodiment of the present invention will be described as follows with reference to FIG. 14. For convenience of description, a member having the same function as that of the member described in the embodiments will be given the same reference numeral, and description thereof will not be repeated.

FIG. 14 is a partially sectional schematic view illustrating a configuration of a support member 13 in the present embodiment and an effect achieved by the configuration. As illustrated in FIG. 14, the support member 13 has a configuration in which an elastic member 13h such as an O-ring is attached to the front end side of the long guide introduction portion 13e of the support member 13 (refer to FIG. 5(a)) of Embodiment 1.

For example, in a case where the support member 13 is supposed to be used for two types of trocars 31 with outer diameters of 5 mm and 3 mm, an outer diameter of the elastic member 13h is required to be smaller than an inner diameter of the trocar 31 with the small diameter of 3 mm.

According to this configuration, in a case where the support member 13 is inclined with respect to the trocar 31, the elastic member 13h comes into contact with the inner wall of the trocar 31 earlier than the front end side of the guide introduction portion 13e. Therefore, inclination of the support member 13 can be suppressed, and thus an angular deviation in the visual field direction can be further reduced. Particularly, in a case where the support member is used in combination with the trocar 31 with the large diameter of 5 mm, it is possible to considerably reduce an angular deviation in the visual field direction more than in the support member 13 of Embodiment 1.

Since friction force between the elastic member 13h and the trocar 31 is large, release from the trocar 31 can be further made to be less likely to occur.

Embodiment 6

Still another embodiment of the present invention will be described as follows with reference to FIG. 15. For convenience of description, a member having the same function as that of the member described in the embodiments will be given the same reference numeral, and description thereof will not be repeated.

FIG. 15 is a partially sectional schematic view illustrating a configuration of a support member 13 in the present embodiment and an effect achieved by the configuration. As illustrated in FIG. 15, the support member 13 has a configuration in which the stepped trocar connection portion 13x of the support member 13 (refer to FIG. 13(a)) of Embodiment 4 is formed of an elastic body. FIG. 15 illustrates a configuration in which the root portion 13z is not provided with the columnar part 13z-1, but the root portion may be provided with the columnar part 13z-1.

With this configuration, in addition to the effect of increasing an area of surface contact between the support member 13 and the inner wall of the trocar 31, the support member and the trocar can be fixed to each other more strongly by elastic force (restoring force) of the elastic body and friction force between the contact surfaces, and thus it is possible to further increase fixation strength.

Embodiment 7

Still another embodiment of the present invention will be described as follows with reference to FIGS. 16 to 23. For convenience of description, a member having the same function as that of the member described in the embodiments will be given the same reference numeral, and description thereof will not be repeated.

Figure 16:
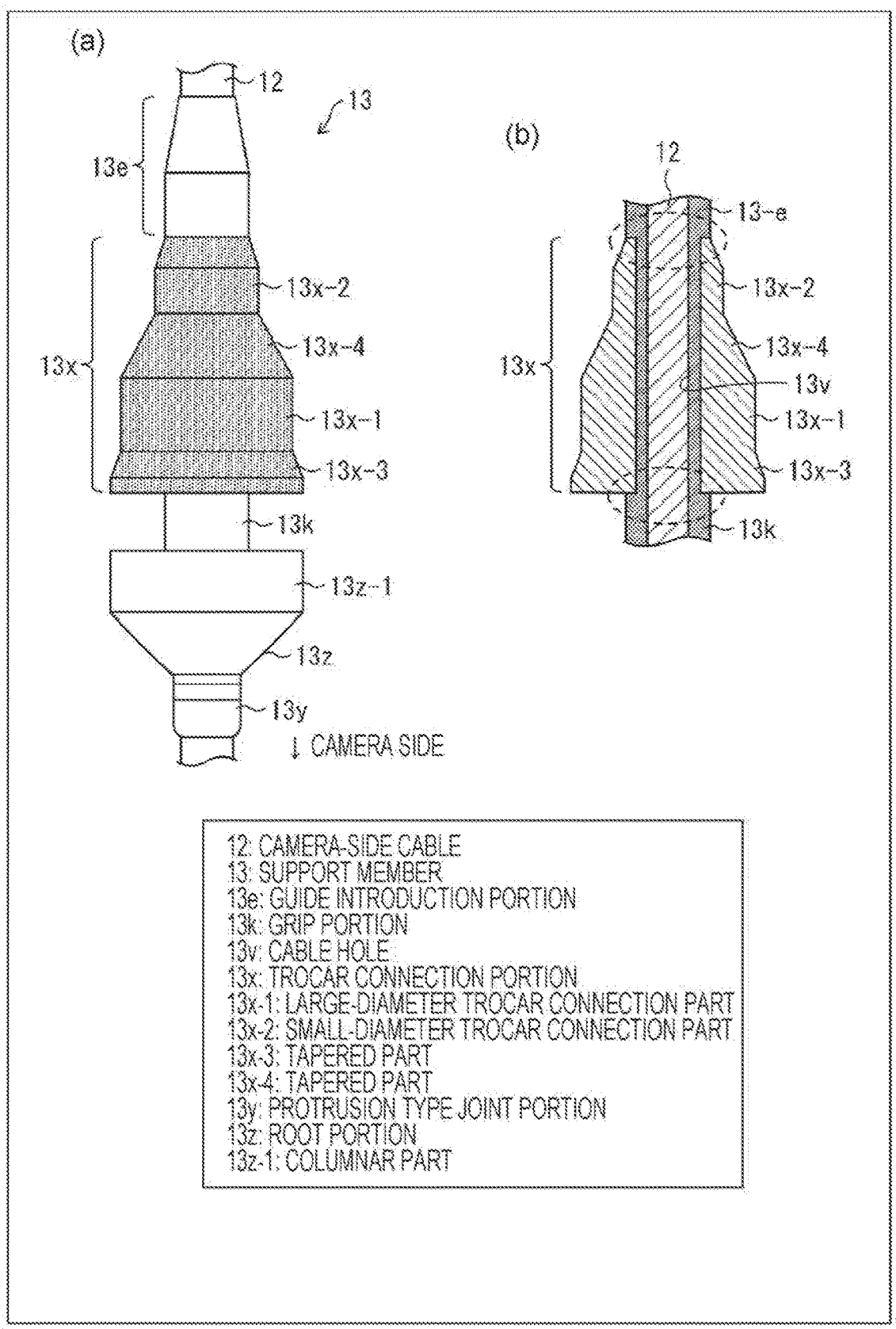
Figure 17:
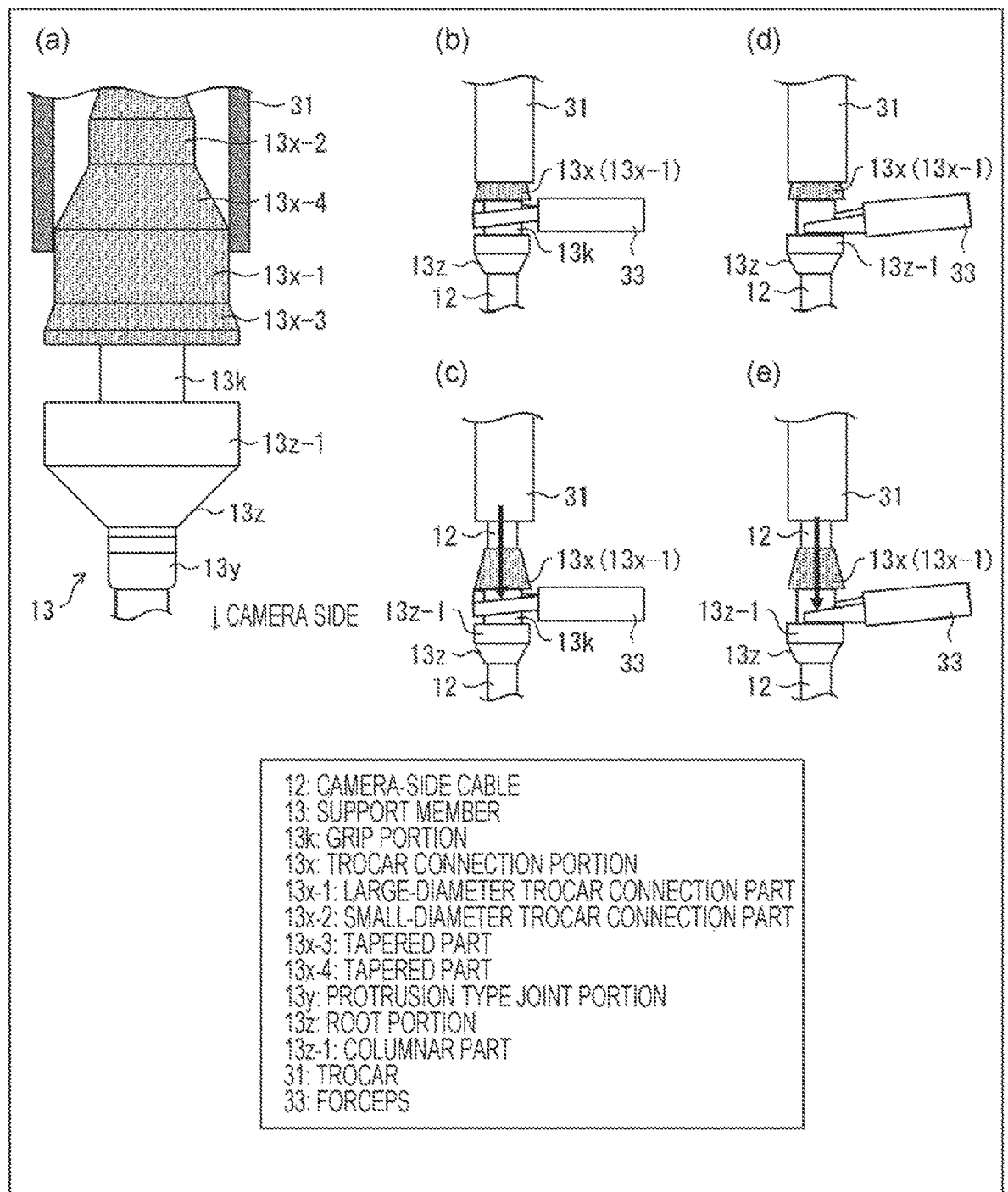
FIG. 17(a) is a sectional view illustrating a configuration of the support member.
FIGS. 17(b) and 17(c) are front views illustrating a state in which a large-diameter trocar connection part is extracted from a trocar by pulling a grip portion of the support member to a camera side while the grip portion is pinched with forceps.
FIGS. 17(d) and 17(e) are front views illustrating a state in which the large-diameter trocar connection part is extracted from the trocar by pushing down a columnar part of the support member with the forceps.
Figure 18:
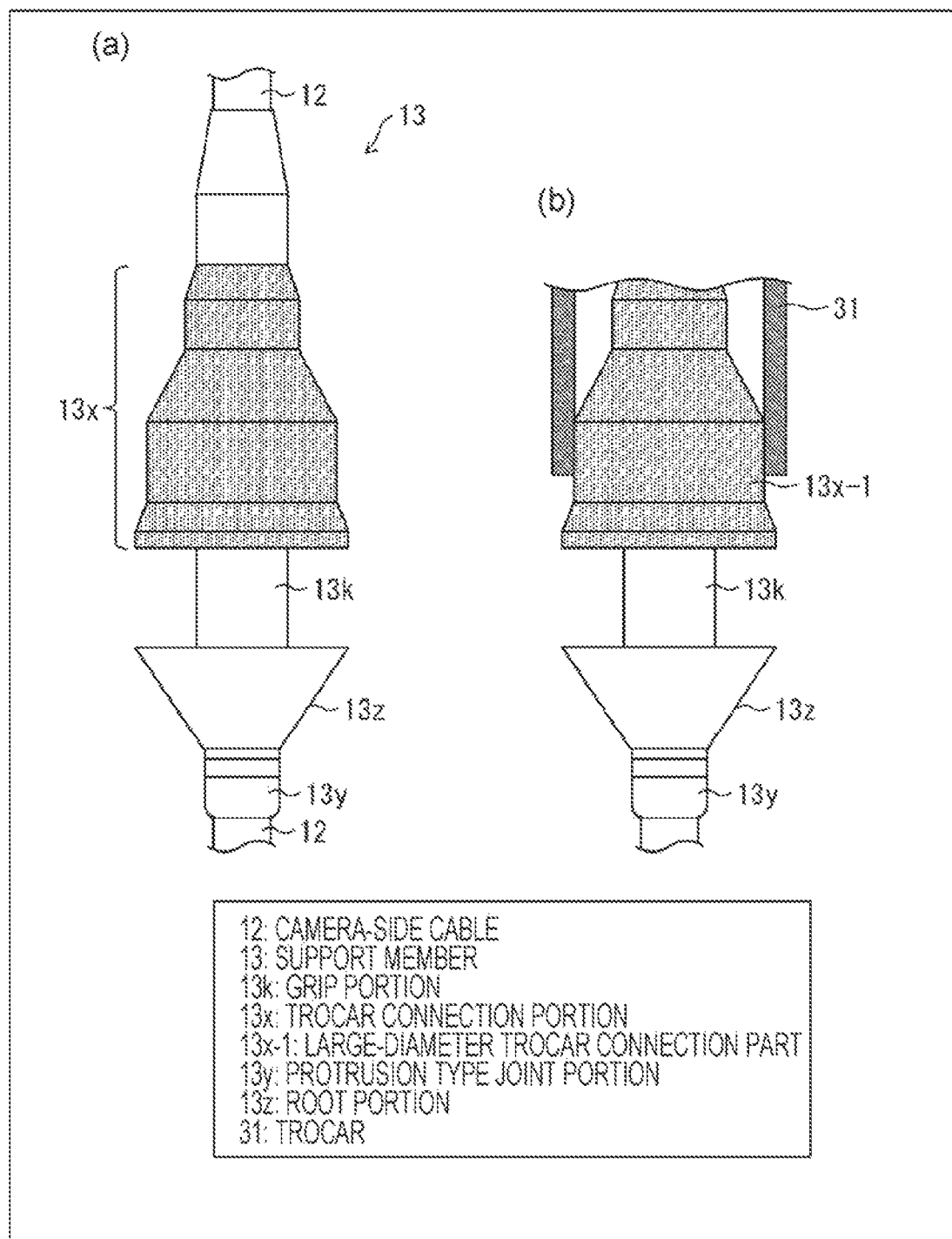
FIG. 18(a) is a front view illustrating a configuration of the support member without the columnar part.
FIG. 18(b) is a sectional view illustrating a configuration of the support member without the columnar part.
Figure 19:
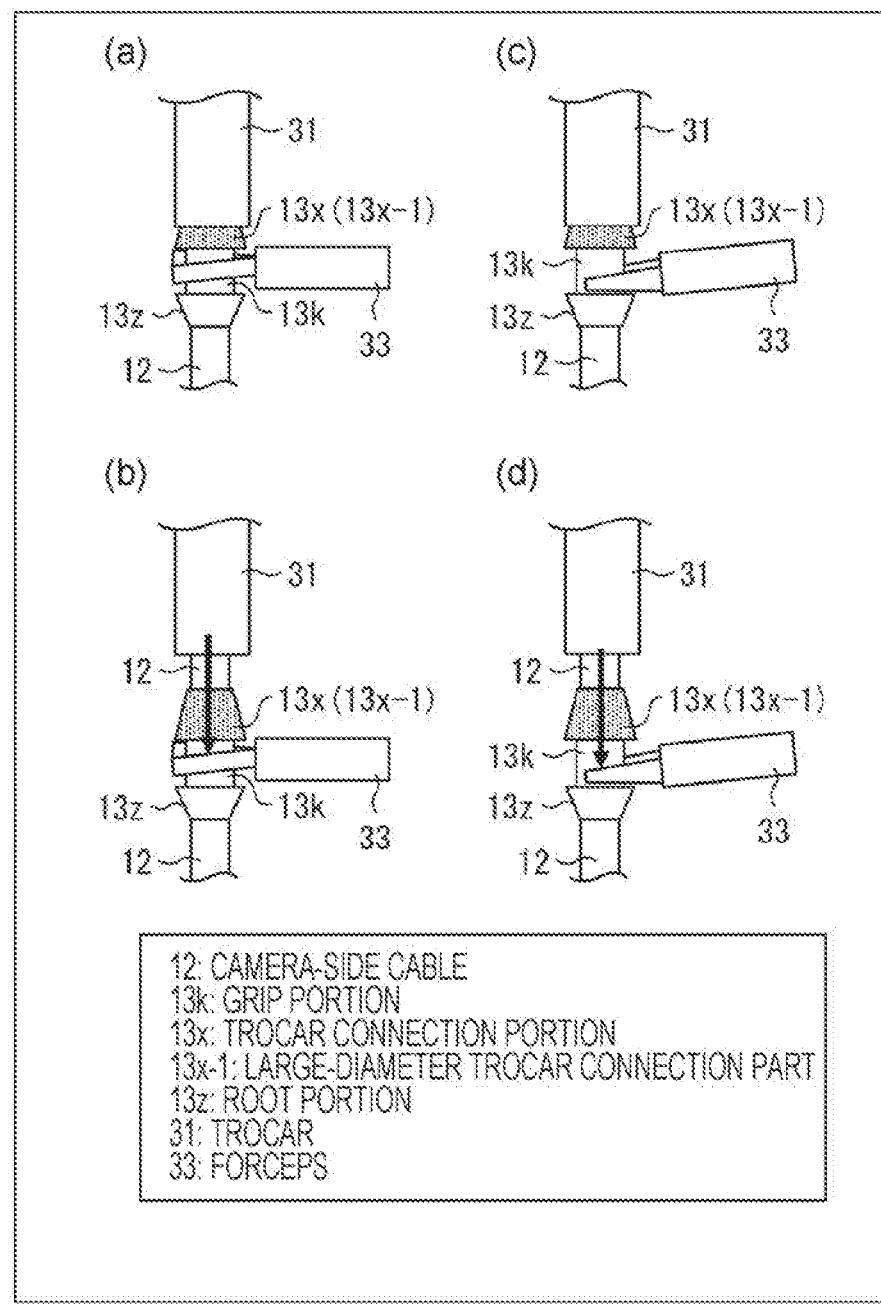
FIGS. 19(a) and 19(b) are front views illustrating a state in which the large-diameter trocar connection part is extracted from the trocar by pulling the grip portion of the support member without the columnar part to the camera side while the grip portion is pinched with the forceps.
FIGS. 19(c) and 19(d) are front views illustrating a state in which the large-diameter trocar connection part is extracted from the trocar by pushing down a root portion of the support member without the columnar part with the forceps.
Figure 20:
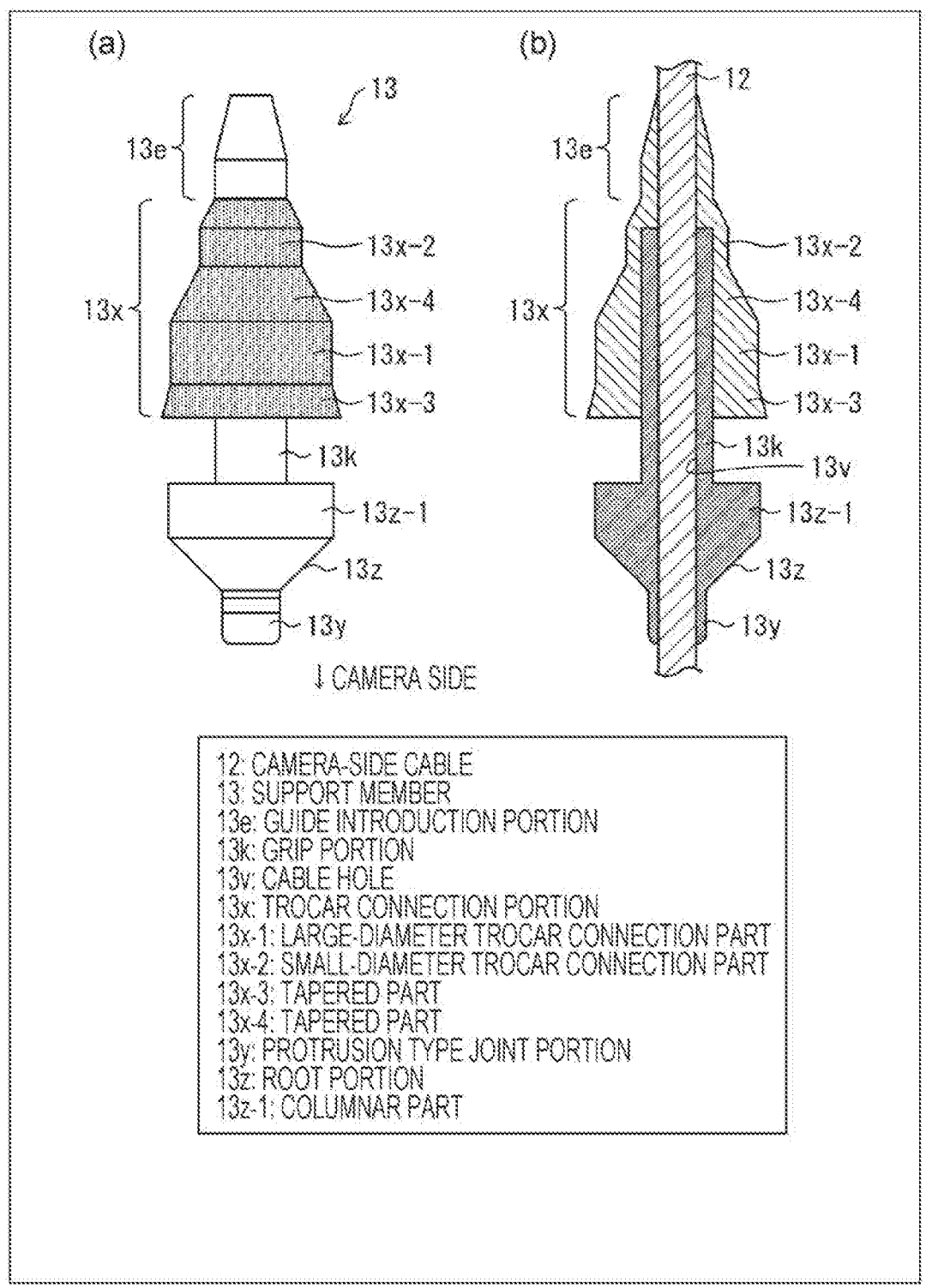
FIGS. 20(a) and 20(b) are respectively a front view and a sectional view illustrating a configuration of the support member of which a guide introduction portion and the trocar connection portion are formed of elastic bodies.
Figure 21:
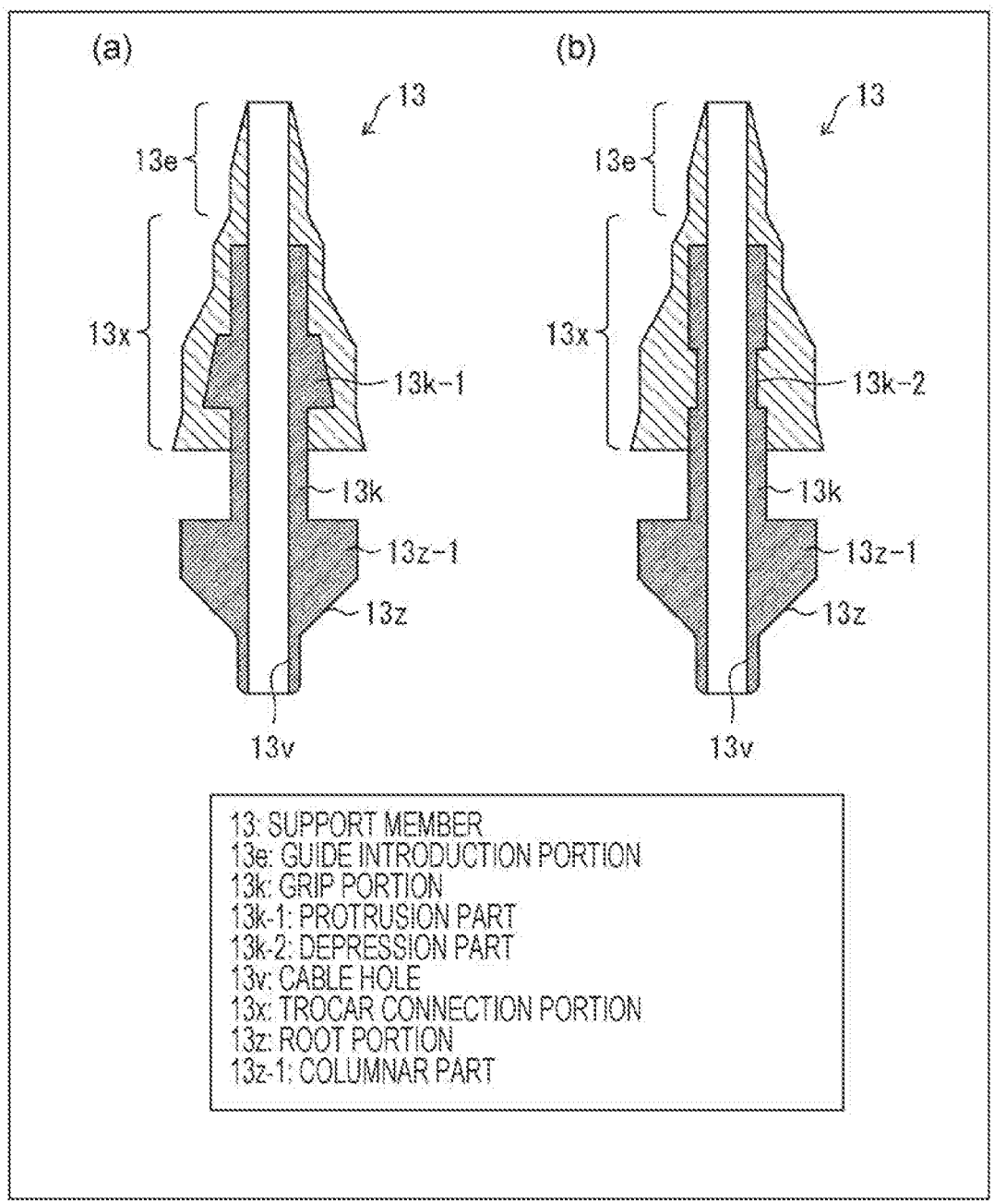
FIG. 21(a) is a sectional view illustrating a configuration of a grip portion provided with a protrusion part in the support member of which the guide introduction portion and the trocar connection portion are formed of elastic bodies.
FIG. 21(b) is a sectional view illustrating a configuration of a grip portion provided with a depression part in the support member of which the guide introduction portion and the trocar connection portion are formed of elastic bodies.
Figure 22:
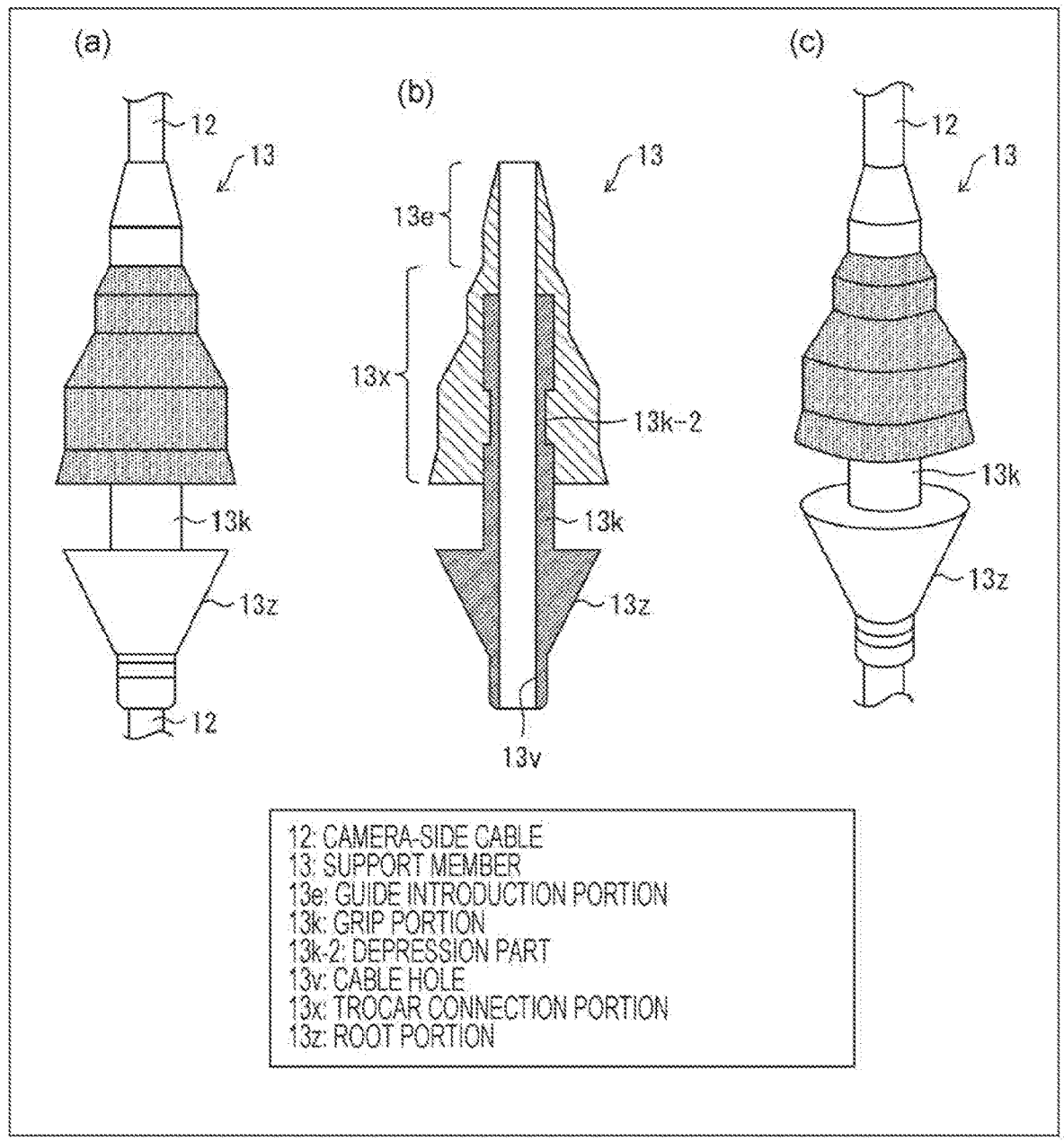
FIGS. 22(a), 22(b), and 22(c) are respectively a front view, a sectional view, and a perspective view illustrating a configuration of a grip portion provided with a depression part in the support member of which the guide introduction portion and the trocar connection portion are formed of elastic bodies and which is not provided with a columnar part.
Figure 23:
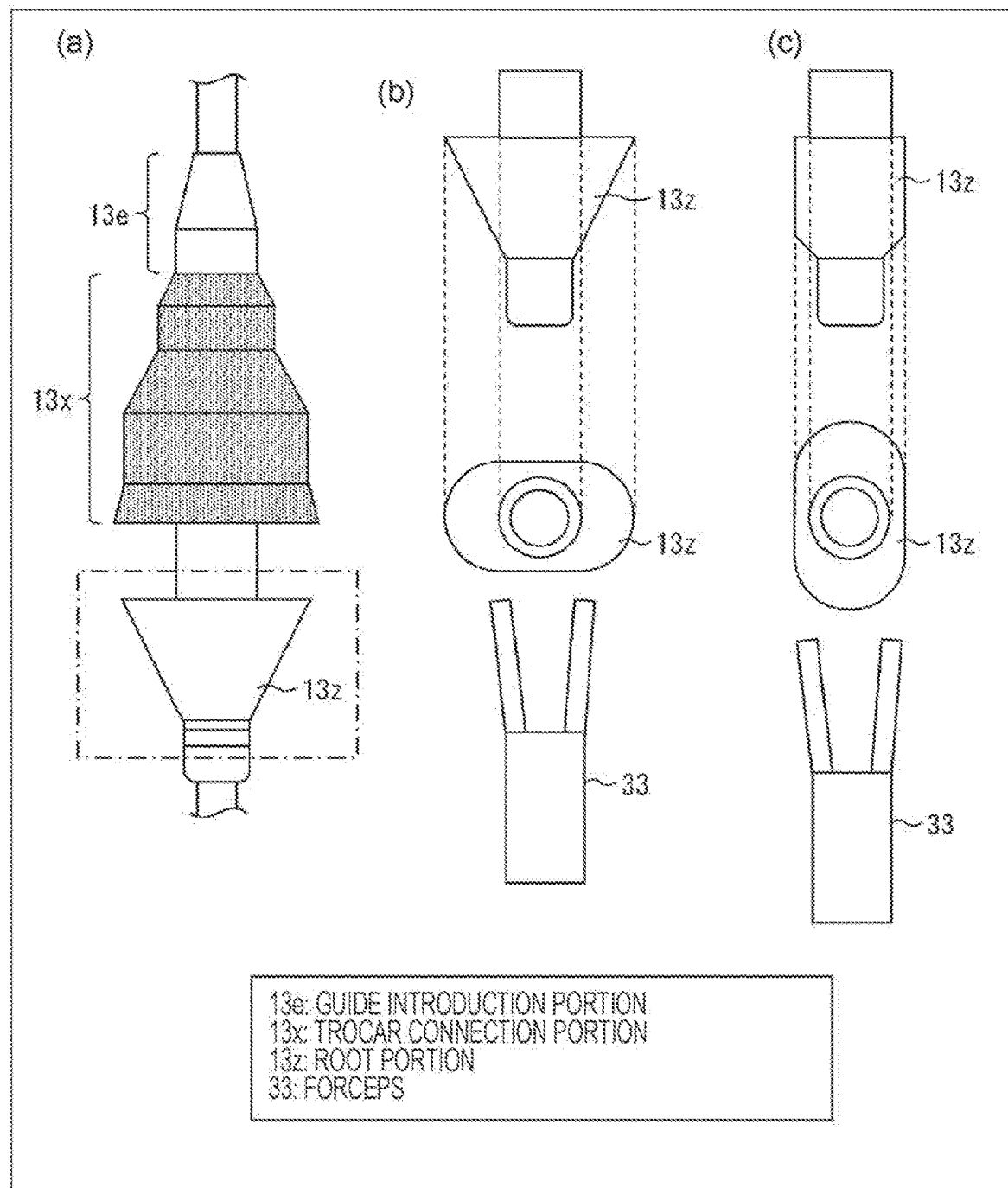
FIG. 23(a) is a front view illustrating a configuration of a support member in which the root portion has functions of the columnar part and the root portion.
FIG. 23(b) is a diagram illustrating a front surface shape thereof.
FIG. 23(c) is a diagram illustrating a side surface shape thereof.

FIG. 16 illustrates still another embodiment, in which FIG. 16(a) is a front view illustrating a configuration of a support member 13, and FIG. 16(b) is a sectional view illustrating main portions of the support member 13. As illustrated in FIGS. 16(a) and 16(b), the support member 13 has a deformed stepped trocar connection portion 13x as a stabilization structure. The support member has a tapered part 13x-4 between the small-diameter trocar connection part 13x-2 and the large-diameter trocar connection part 13x-1 corresponding to a plurality of columnar parts being coaxial with each other. The tapered part 13x-4 spreads from the rear end of the small-diameter trocar connection part 13x-2. A tapered part 13x-3 is provided at the rear end of the large-diameter trocar connection part 13x-1. The tapered part 13x-3 spreads from the rear end of the large-diameter trocar connection part 13x-1.

The tapered part 13x-4 functions as a stopper that butts with the front end of the trocar 31 with an inner diameter size slightly larger than that of the small-diameter trocar connection part 13x-2 and stops the trocar. The tapered part 13x-3 functions as a stopper that butts with the front end of the trocar 31 with an inner diameter size slightly larger than that of the large-diameter trocar connection part 13x-1 and stops the trocar. The trocar connection portion 13x is formed of an elastic body, and thus connection surfaces between the tapered parts 13x-3 and 13x-4 and the trocar 31 can be subjected to surface contact.

The guide introduction portion 13e has a columnar shape, and the front end thereof is formed to be thin. With this shape, the front end can be smoothly introduced into the trocar 31.

A grip portion 13k with a small diameter is provided between the trocar connection portion 13x and the columnar part 13z-1. When the support member 13 is detached from the trocar 31, the grip portion 13k is gripped with forceps, and thus detachment can be easily performed.

Specifically, as illustrated in FIG. 17(a), the support member 13 is fixed to the trocar 31 via the large-diameter trocar connection part 13x-1. In a case where the large-diameter trocar connection part 13x-1 is detached from the trocar 31 in this state, for example, as illustrated in FIGS. 17(b) and 17(c), the grip portion 13k is pulled toward the camera side by pinching the grip portion 13k with the forceps 33. Consequently, the large-diameter trocar connection part 13x-1 can be extracted from the trocar 31. Alternatively, as illustrated in FIGS. 17(d) and (e), the forceps 33 catch the columnar part 13z-1 under the grip portion 13k, and push the columnar part 13z-1 toward the camera side. Consequently, the large-diameter trocar connection part 13x-1 can be extracted from the trocar 31.

Here, in a case where the large-diameter trocar connection part 13x-1 is detached from the trocar 31 by pinching the grip portion 13k with the forceps 33, for example, as illustrated in FIGS. 18(a) and (b), the columnar part 13z-1 may not be present over the root portion 13z in the support member 13. In this case, as illustrated in FIGS. 19(a) and 19(b), the grip portion 13k is pulled toward the camera side by pinching the grip portion 13k with the forceps 33, and thus the large-diameter trocar connection part 13x-1 can be extracted from the trocar 31.

Alternatively, as illustrated in FIGS. 19(a) and (b), the forceps 33 catch the root portion 13z under the grip portion 13k, and push the root portion 13z toward the camera side. Consequently, the large-diameter trocar connection part 13x-1 can be extracted from the trocar 31.

In the example illustrated in FIGS. 16(a) and 16(b), the guide introduction portion 13e to the protrusion type joint portion 13y are formed of an integrated resin molding, and, as illustrated in FIGS. 20(a) and 20(b), the trocar connection portion 13x formed of an elastic body is attached to the resin molding. In this case, as illustrated in FIG. 16(b), a portion of the resin molding attached with the trocar connection portion 13x is preferably provided with a step difference such that the elastic body is not extracted. Instead of the step difference, something like a turn (not illustrated) may be provided at a location indicated by the dotted O in FIG. 16(b).

As illustrated in FIGS. 20(a) and 20(b), not only the guide introduction portion 13e but also the inside of the trocar connection portion 13x reaching the cable hole 13v may be formed of an elastic body. Consequently, when the support member 13 is connected to the trocar 31, pressure applied to the trocar connection portion 13x is also applied to the cable hole 13v, and thus the inner wall of the cable hole 13v and the camera-side cable 12 are brought into close contact with each other. Consequently, since the camera-side cable 12 is less likely to be slid on the cable hole 13v, there is an effect that, even in a case where joint between the support member 13 and the camera unit 11 is released during an operation, the camera-side cable 12 restricts movement of the camera unit 11, and thus a probability of a visual field being changed is reduced.

In the example illustrated in FIGS. 20(a) and 20(b), the guide introduction portion 13e and the trocar connection portion 13x are formed of an integrated resin molding and is formed of an elastic body. In this case, when the guide introduction portion 13e and the trocar connection portion 13x are simply attached to the grip portion 13k, there is concern that the guide introduction portion 13e and the trocar connection portion 13x may be extracted from the grip portion 13k. Therefore, for example, as illustrated in FIG. 21(a), preferably, the grip portion 13k is provided with a protrusion part 13k-1, and the trocar connection portion 13x is provided with a depression part fitted to the protrusion part 13k-1. Consequently, the guide introduction portion 13e and the trocar connection portion 13x can be prevented from being easily extracted from the grip portion 13k. Alternatively, as illustrated in FIG. 21(b), preferably, the grip portion 13k is provided with a depression part 13k-2, and the trocar connection portion 13x is provided with a protrusion part fitted to the depression part 13k-2. Consequently, the guide introduction portion 13e and the trocar connection portion 13x can also be prevented from being easily extracted from the grip portion 13k.

Here, for example, as illustrated in FIGS. 22(a), 22(b), and 22(c), the type illustrated in FIG. 21(b) may be employed in the type in which the columnar part 13z-1 is not present under the root portion 13z illustrated in FIGS. 18(a) and 18(b). Consequently, even in the type in which the columnar part 13z-1 is not present, the guide introduction portion 13e and the trocar connection portion 13x can be prevented from being easily extracted from the grip portion 13k.

As illustrated in FIGS. 16(a) and 16(b), in a case where even the inside of the trocar connection portion 13x reaching the cable hole 13v is formed of an elastic body, the middle of a portion to which the trocar connection portion 13x is attached may be formed of the resin molding, and the trocar connection portion 13x formed of an elastic body may be attached thereto along with the guide introduction portion 13e. As another configuration, the grip portion 13k to the protrusion type joint portion 13y may be formed of the resin molding, and the guide introduction portion 13e to the trocar connection portion 13x may be all formed of an elastic body. The embodiment does not limit a portion formed of a resin or an elastic body, and all remaining portions may be formed of an elastic body except the protrusion type joint portion 13y required to have some extent of hardness, in order to be joined to the camera unit 11, and the root portion 13z of which the surface is required to be made of a material slidable to some extent in order to cancel joint between the camera unit 11 and the support member 13. Each portion of the support member 13 may be selectively formed of an elastic body depending on purposes.

In a case where the trocar connection portion 13x is formed of an elastic body, the elastic body with a shape may be attached to a resin component, and the elastic body is also molded when the resin component is manufactured such that the elastic body and the resin component may be manufactured together.

In the present embodiment, in FIG. 16, the name corresponding to the function of each portion of the components of the support member 13 is written, but a single portion having two or more functions may be provided, and an integrated component may have a plurality of functions even though a separate component is formed for each function. For example, as indicated by a dot chain line in FIG. 23(a), the function of the grip portion 13k and the function of the root portion 13z (refer to Embodiment 2) illustrated in FIG. 10 may be integrated into one. Specifically, the root portion 13z may have the function of the grip portion 13k from a specific direction, and may have the function of the root portion 13z when approached from another specific direction. For example, as illustrated in FIG. 23(b), since the root portion 13z has a trapezoidal shape when viewed from the front, the tapered part of the root portion 13z is pinched with the forceps 33 and is slid to be raised and pulled away from the camera unit 11, and thus the support member 13 and the camera unit 11 can be easily separated from each other. On the other hand, as illustrated in FIG. 23(c), the root portion 13z has a parallel surface as each of both right and left surfaces. Thus, the support member 13 can be released from the trocar 31 by pinching the parallel surfaces of the root portion 13z with the forceps 33.

Alternatively, the function of the columnar part 13z-1 may also be integrated into one.

Embodiment 8

Still another embodiment of the present invention will be described as follows with reference to FIGS. 24 to 28. For convenience of description, a member having the same function as that of the member described in the embodiments will be given the same reference numeral, and description thereof will not be repeated.

In the present embodiment, a description will be made of a cable holder that applies tensile force to the camera-side cable 12 and thus fixes the camera-side cable 12.

Example 1 of Cable Holder

Figure 24:
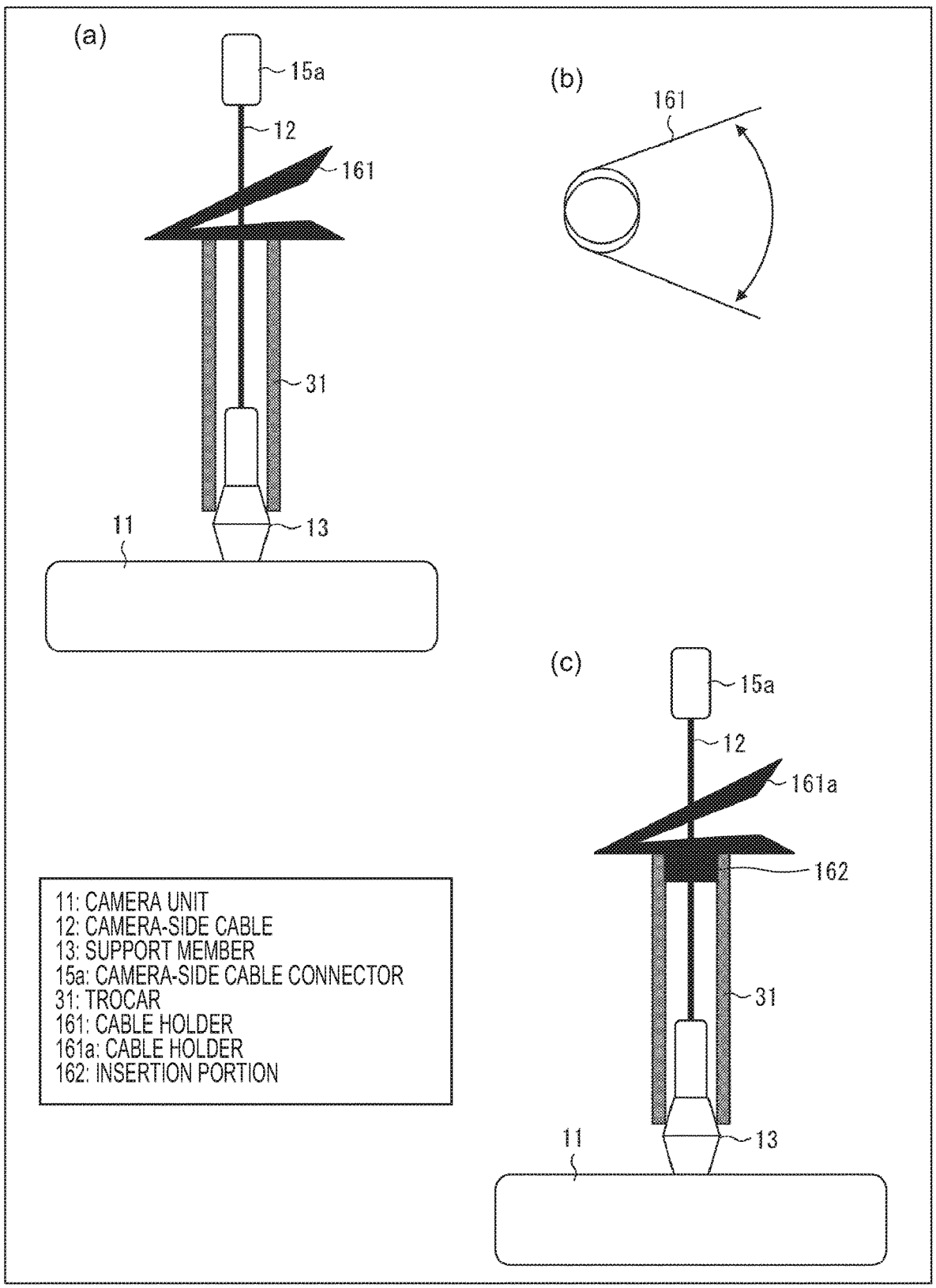
FIG. 24 illustrates still another embodiment of the present invention, and is a diagram illustrating an example of a cable holder.

FIG. 24 is a diagram illustrating an example of a cable holder according to the present embodiment. In other words, the cable holder may be a cable holder 161 illustrated in FIGS. 24(a) and 24(b). The cable holder 161 is a spring or a clip that holds the camera-side cable 12 at the end of the trocar 31 on the outer side of the body, and applies elastic force in an opening direction. A structure of a portion of the cable holder 161 fixing the camera-side cable 12 is not particularly limited as long as the camera-side cable 12 can be fixed. However, a structure is preferably used in which an operator can fix the camera-side cable 12 in a single operation.

The cable holder may be a cable holder 161a illustrated in FIG. 24(c). The cable holder 161a is the cable holder 161 provided with an insertion portion 162 that is a projection insertable into the trocar 31. As illustrated in FIG. 24(c), the insertion portion 162 is inserted into the trocar 31, and thus the cable holder 161a can be stably attached to the end of the trocar 31, and a gas inside of the body can be prevented from leaking to the outside of the body through the trocar 31.

Example 2 of Cable Holder

Figure 25:
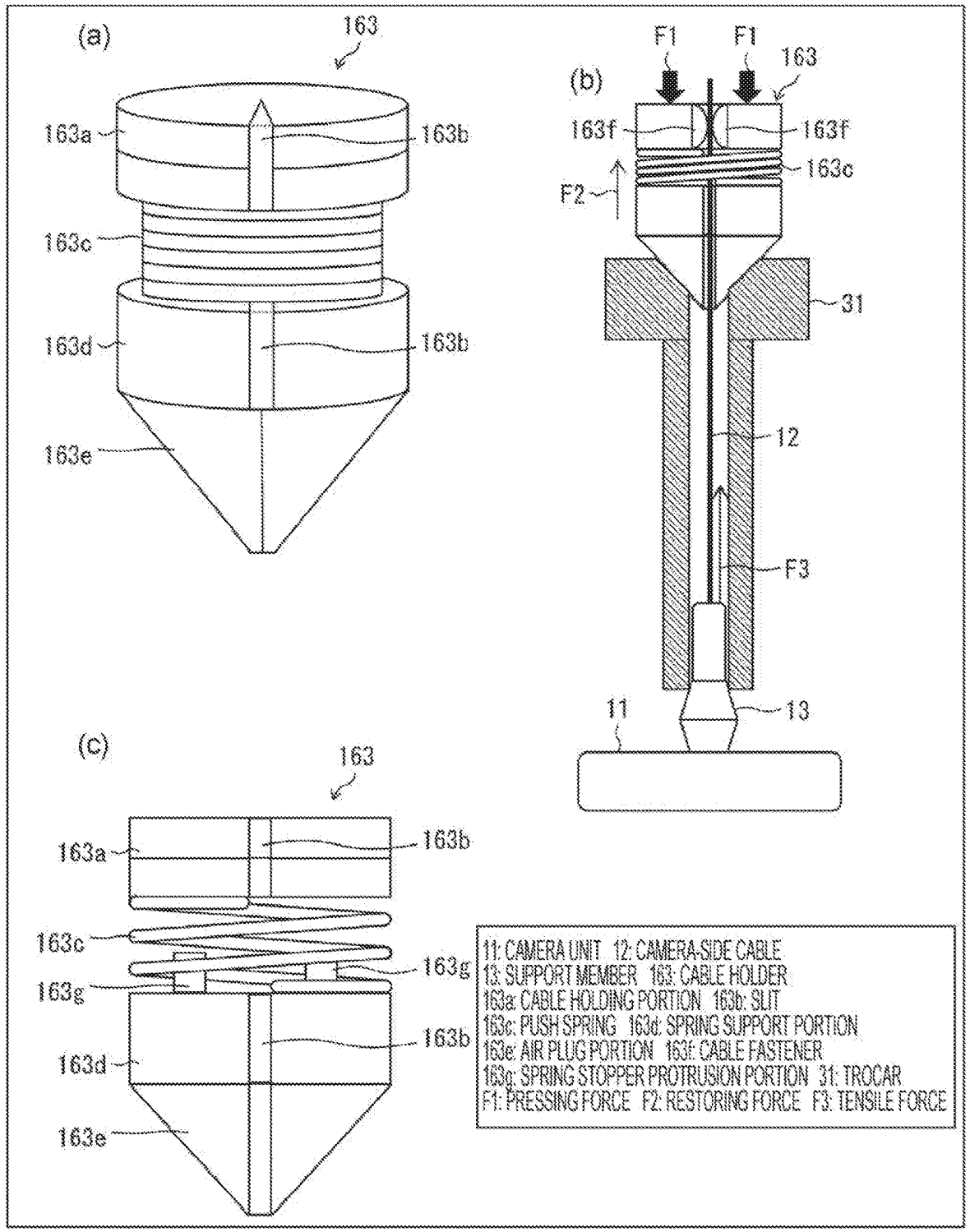
FIG. 25 illustrates another example of the cable holder.

The cable holder is not limited to a spring or a clip as illustrated in FIG. 24. For example, the cable holder may be a cable holder 163 illustrated in FIG. 25. FIG. 25 is a diagram illustrating another example of a cable holder according to the present embodiment.

As illustrated in FIG. 25(a), the cable holder 163 is provided with a cable holding portion 163a, a push spring 163c, a spring support portion 163d, and an air plug portion 163e.

The cable holding portion 163a and the spring support portion 163d are disk-shaped (columnar) members are provided with a slit 163b into which the camera-side cable 12 is inserted. The cable holding portion 163a and the spring support portion 163d are made of a material such as a resin. The slit 163b is provided along axes of the cable holding portion 163a and the spring support portion 163d, and has a depth reaching the centers of the cable holding portion 163a and the spring support portion 163d. A width of the slit 163b is equal to or more than a diameter of the camera-side cable 12 (more than at least a minor axis of a section of the camera-side cable 12) from an outer circumferential side to the center thereof in the spring support portion 163d. Consequently, an operator can insert the camera-side cable 12 into the center of the spring support portion 163d from the slit 163b.

On the other hand, in the cable holding portion 163a, the width of the slit 163b is equal to or more than a diameter of the camera-side cable 12 on the outer circumferential side in the same manner as in the spring support portion 163d, but is less than the diameter of the camera-side cable 12 at the center thereof. Consequently, the camera-side cable 12 is tightened at the center of the cable holding portion 163a such that the camera-side cable 12 is restricted to be moved along the axial direction, and thus the camera-side cable 12 can be fixed to the cable holding portion 163a.

A fixing mechanism for the camera-side cable 12 using the slit 163b is only an example, and the cable holding portion 163a may be provided with a mechanism (hereinafter, referred to as a hold mechanism) fixing the camera-side cable 12.

The push spring 163c is disposed between the cable holding portion 163a and the spring support portion 163d. The push spring 163c is generally made of metal, but may be made of a resin in a case where there is concern that noise may occur in an image captured by the camera unit 11.

The air plug portion 163e is a plug that is disposed on the rear surface side of the spring support portion 163d and prevents a gas inside of the body from leaking to the outside of the body through the support member 13. As illustrated in FIG. 25(a), the air plug portion 163e has a conic shape, and is made of a material such as rubber or sponge. Consequently, the air plug portion 163e can close the end of the support member 13 on the outer side of the body.

An insertion hole (not illustrated) through which the camera-side cable 12 passes is provided at the center of the air plug portion 163e. As illustrated in FIG. 25(a), the air plug portion 163e is also provided with a slot at a position corresponding to the slit 163b. Consequently, the camera-side cable 12 can also be inserted into the air plug portion 163e. Since the air plug portion is made of a material such as rubber or sponge, a width of the slot can be made less than the diameter of the camera-side cable 12, and thus it is possible to prevent a gas inside of the body from leaking out of the slot.

FIG. 25(b) is a diagram illustrating an example of fixation of the camera-side cable 12 using the cable holder 163. In FIG. 25(b), the cable holding portion 163a is provided with a hold mechanism different from that illustrated in FIG. 25(a). In other words, cable fasteners 163f are provided as the hold mechanism. A pair of cable fasteners 163f are provided to face each other on both wall surfaces of the slit 163b at the center of the cable holding portion 163a. The cable fasteners 163f pinch the camera-side cable 12 between facing surfaces so as to fix the camera-side cable 12.

As illustrated, an operator presses the air plug portion 163e against the trocar 31 from the upper side of the cable holding portion 163a. In other words, pressing force F1 for pressing the air plug portion 163e against the support member 13 is applied to the cable holding portion 163a. Consequently, the push spring 163c is shrunk, and thus the cable holding portion 163a is moved toward the trocar 31 side (the downward direction in the figure). In this state, the camera-side cable 12 inserted into the air plug portion 163e and the center of the spring support portion 163d is inserted into the center of the cable holding portion 163a by using the slit 163b, and is fixed by the cable fasteners 163f. Thereafter, when the operator stops to apply the pressing force F1, the cable holding portion 163a is moved in the upward direction by restoring force F2 (elastic force) of the push spring 163c. Consequently, tensile force F3 is applied to the camera-side cable 12 fixed to the cable holding portion 163a, and thus the camera-side cable 12 is fixed in a stretched state.

The cable holder 163 according to the present embodiment may be provided with spring stopper protrusion portions 163g as illustrated in FIG. 25(c). The spring stopper protrusion portions 163g are projections provided on the upper surface of the spring support portion 163d. The spring stopper protrusion portions 163g are provided, and thus a limit of shrinkage of the push spring 163c can be set. In other words, the spring stopper protrusion portions 163g are provided, and thus the maximum value of restoring force of the push spring 163c can be set.

Figure 26:
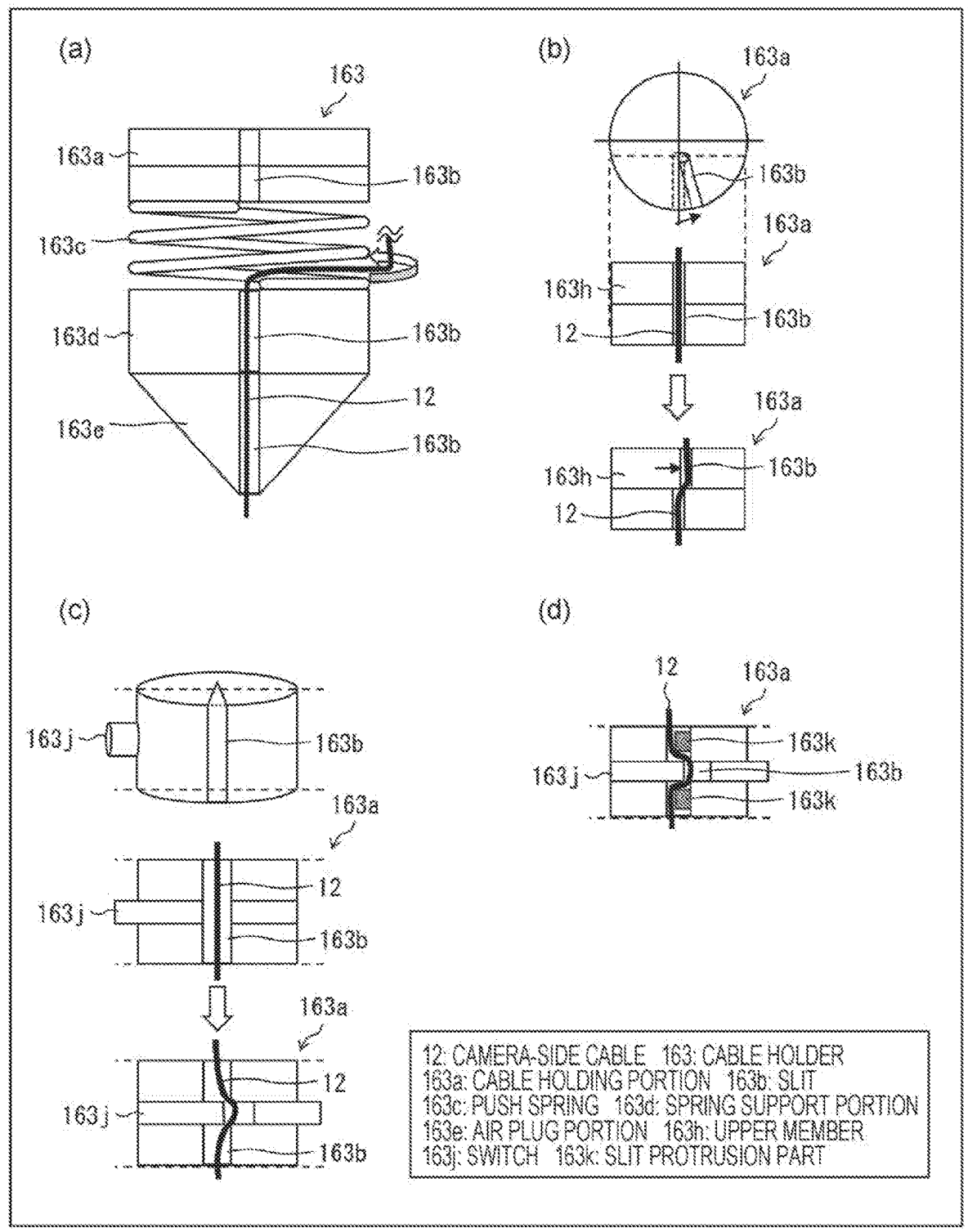
FIG. 26 is a diagram illustrating details of the cable holder illustrated in FIG. 25.

FIG. 26 is a diagram illustrating details of the cable holder 163. FIG. 26(a) is a diagram illustrating an example of a method of causing the camera-side cable 12 to pass through the center of the push spring 163c. As illustrated, an operator inserts the camera-side cable 12 into the slit 163b of the spring support portion 163d, and then puts the camera-side cable 12 in the push spring 163c from the side surface thereof. The operator winds the camera-side cable to pass through a gap of the push spring 163c in accordance with a winding direction of the push spring 163c.

Consequently, the operator can cause the camera-side cable 12 to pass through the center of the push spring 163c.

The cable holder 163 may be provided with a hold mechanism different from that of the above-described example. For example, as illustrated in FIG. 26(b), the cable holding portion 163a of the cable holder 163 may be divided into upper and lower members, and an upper member 163h may be rotated in an outer circumferential direction. Consequently, the operator inserts the camera-side cable 12 into the slit 163b of the cable holding portion 163a, and then rotates the upper member 163h such that the camera-side cable 12 is pinched and fixed between the upper member 163h and the lower member as illustrated. In this case, a width of the slit 163b may be equal to or more than a diameter of the camera-side cable 12 in the same manner as in the spring support portion 163*d* from the outer circumferential side to the center thereof.

For example, as illustrated in FIG. 26(*c*), the cable holding portion 163*a* may be provided with a switch 163*j*. The cable holding portion 163*a* is formed in three stages as illustrated, and is configured such that the middle stage is deviated relative to the upper and lower stages by pushing the switch 163*j*. Consequently, a portion of the slit 163*b* corresponding to the middle stage is deviated as illustrated, and thus the camera-side cable 12 is pinched and fixed. In this case, a width of the slit 163*b* may be equal to or more than a diameter of the camera-side cable 12 in the same manner as in the spring support portion 163*d* from the outer circumferential side to the center thereof.

For example, as illustrated in FIG. 26(*d*), in a case where the cable holding portion is formed in three stages, the cable holding portion 163*a* may be provided with slit protrusion parts 163*k* on side surfaces of portions of the slit 163*b* corresponding to the upper and lower stages. Consequently, the cable holding portion 163*a* can more reliably fix the camera-side cable 12.

Each of the hold mechanisms illustrated in FIGS. 26(*b*) to 26(*d*) may be interlocked with the push spring 163*c*. Specifically, there may be a configuration in which the hold mechanism is in a state of not fixing the camera-side cable 12 when the push spring 163*c* is shrunk by the pressing force, and is in a state of fixing the camera-side cable 12 when the pressing force stops to be applied (right before the push spring 163*c* is returned (before the push spring is expanded)).

Example 3 of Cable Holder

Figure 27:
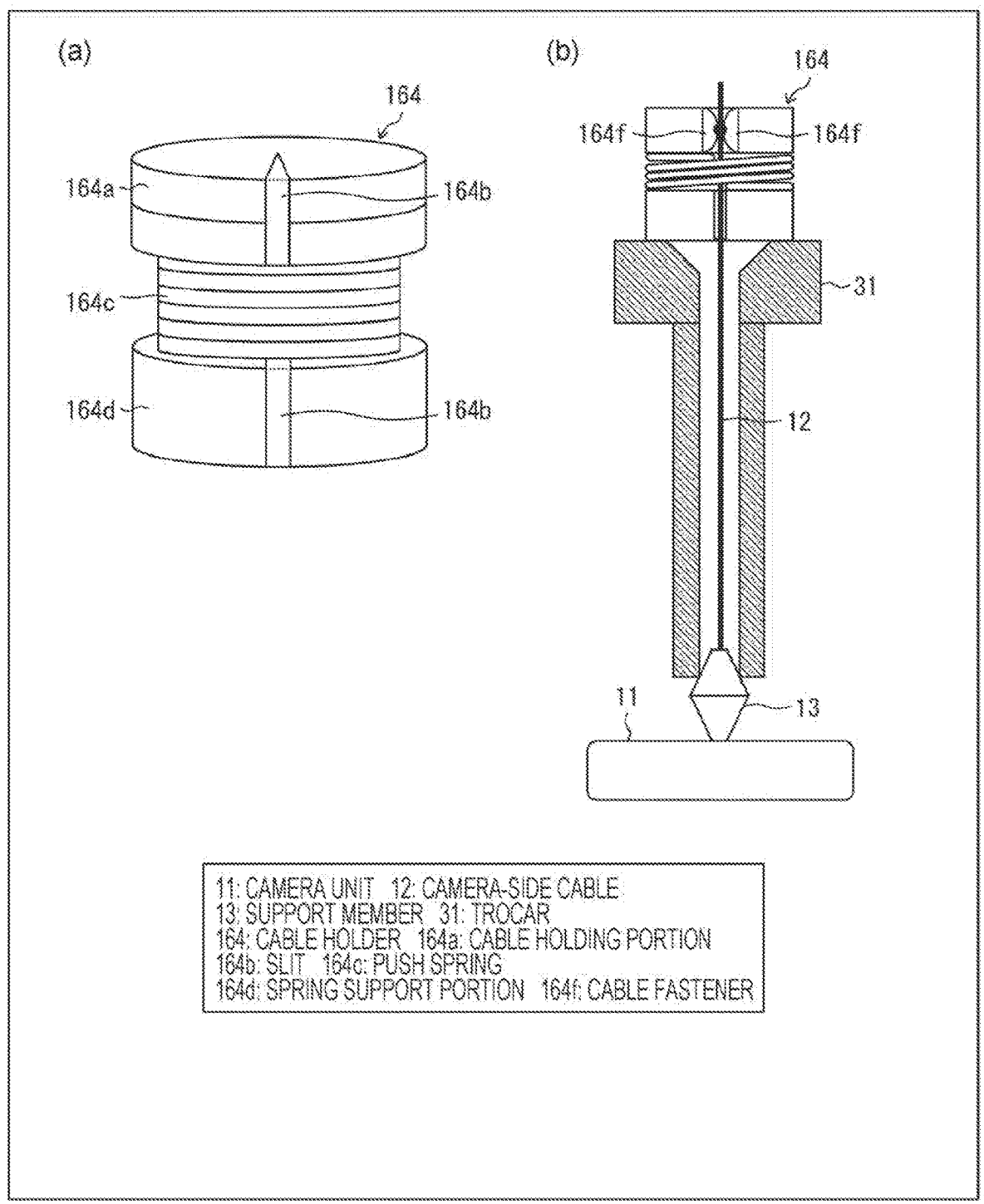
FIG. 27 illustrates still another example of the cable holder.

FIG. 27 is a diagram illustrating still another example of a cable holder according to the present embodiment. As illustrated in FIG. 27(*a*), the cable holder may be a cable holder 164 not provided with the air plug portion 163*e*.

For example, as illustrated in FIG. 11, in a case of the support member 13 of which the trocar connection portion 13*x* is formed of an elastic body or the like, the trocar connection portion 13*x* and the trocar 31 are fitted to each other without a gap, and thus a gas inside of the body does not leak such that the air plug portion 163*e* is not necessary. The cable holder 164 may be used in this case. Each member of the cable holder 164 in this figure has the same function as that of a member having the same number of the cable holder 163, and thus a description thereof will not be repeated here.

Example 4 of Cable Holder

Figure 28:
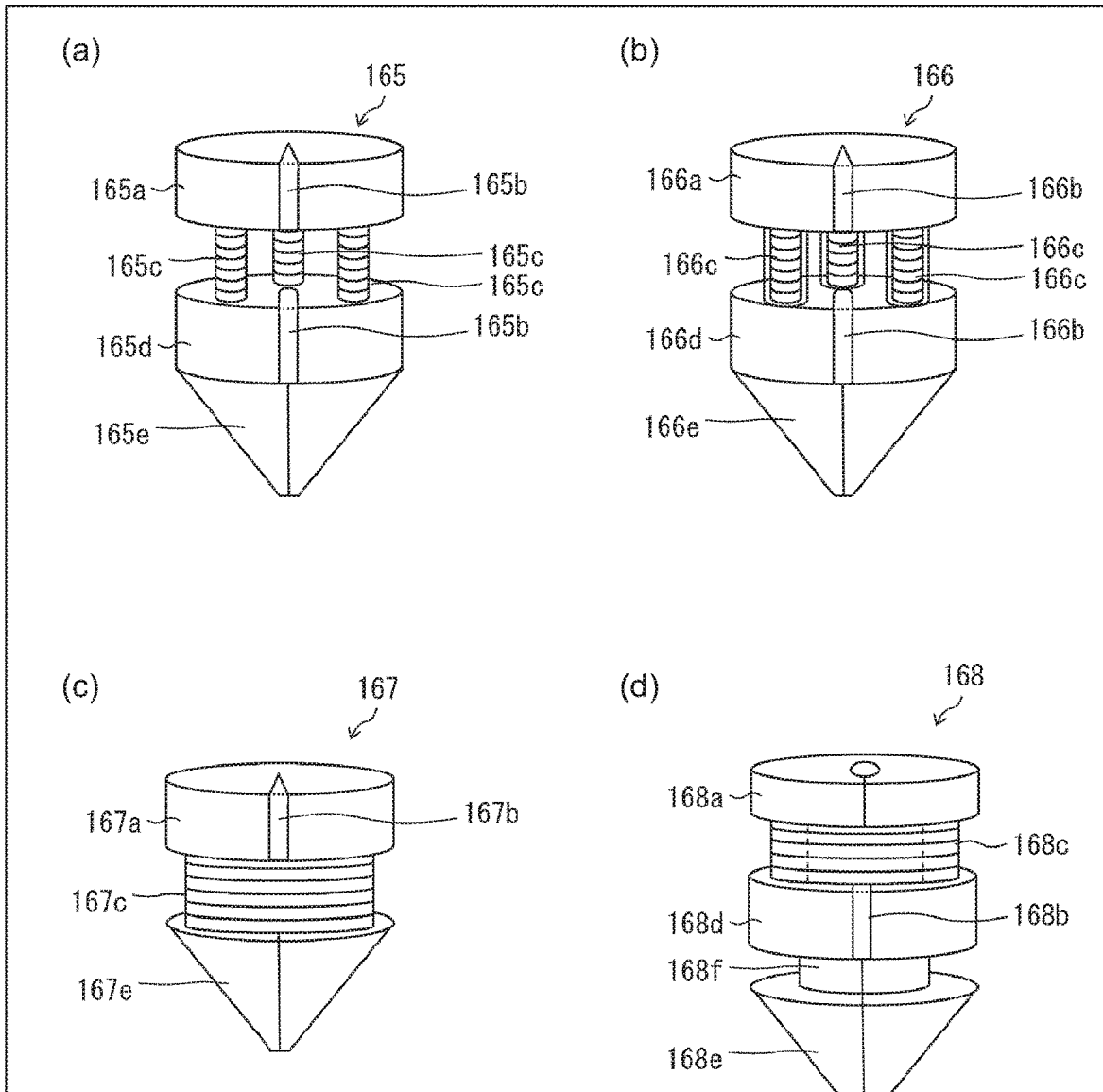
FIG. 28 illustrates still another example of the cable holder.

FIG. 28 is a diagram illustrating still another example of a cable holder according to the present embodiment. Among members illustrated in this figure, a member having the same function as that of each member of the above-described cable holders, will not be described here.

The cable holder may be provided with a plurality of push springs 165*c* instead of the push spring 163*c*, such as a cable holder 165 illustrated in FIG. 28(*a*). Consequently, in a case where the cable holder 165 is used, an operator may have only to insert the camera-side cable 12 into a slit 165*b*. In other words, it is not necessary for the operator to cause the camera-side cable 12 to pass through the push spring in such a method as described with reference to FIG. 26(*a*). As in a cable holder 166 illustrated in FIG. 28(*b*), a plurality of push springs may be push springs 166*c* covered with a resin or the like. The resin or the like used for the push springs 166*c* is a material that does not influence restoring force, and covers the push springs in a method that does not influence the restoring force.

The cable holder may have a configuration in which a push spring 167*c* and an air plug portion 167*e* are directly connected to each other without using a portion corresponding to the spring support portion 163*d*, such as a cable holder 167 illustrated in FIG. 28(*c*).

The cable holder may be provided with a pull spring 168*c* instead of a push spring, such as a cable holder 168 illustrated in FIG. 28(*d*). As illustrated, a spring support portion 168*a* is located above, and a cable holding portion 168*d* is located thereunder. The pull spring 168*c* is disposed between the spring support portion 168*a* and the cable holding portion 168*d*, one end thereof is connected to the spring support portion 168*a*, and the other end thereof is connected to the cable holding portion 168*d*. The pull spring 168*c* is generally made of metal, but may be made of a resin in a case where there is concern that noise may occur in an image captured by the camera unit 11.

As described above, the spring support portion 168*a* is connected to one end of the pull spring 168*c*, and is provided with an insertion hole through which the camera-side cable 12 passes at the center thereof along the axis (not illustrated). A slot is provided at a position corresponding to a slit 168*b*. Consequently, the camera-side cable 12 can be inserted into the center of the spring support portion 168*a*.

The cable holding portion 168*d* is formed in an annular shape here. A part provided with the slit 168*b* in the cable holding portion 168*d* extends toward the center, and the extending part is provided with an insertion hole through which the camera-side cable 12 passes and a hold mechanism.

The cable holder 168 includes a guide shaft 168*f*. The guide shaft 168*f* is a columnar member provided between the spring support portion 168*a* and an air plug portion 168*e*, and is inserted into the pull spring 168*c* and the cable holding portion 168*d*. The guide shaft 168*f* is provided with an insertion hole through which the camera-side cable 12 passes. The guide shaft 168*f* is provided with a groove (not illustrated) extending in the axial direction in correspondence to the extending part of the cable holding portion 168*d*. The extending part of the cable holding portion 168*d* is moved in the axial direction along the groove, and the insertion hole provided in the extending part and the insertion hole provided in the guide shaft 168*f* linearly communicate with each other. The guide shaft 168*f* is provided with a slot at a position corresponding to the slit 168*b*. Consequently, the camera-side cable 12 inserted into the slit 168*b* can also be inserted into the guide shaft 168*f*.

Here, a description will be made of fixation of the camera-side cable 12 using the cable holder 168. The cable holding portion 168*d* is pushed down, and thus the pull spring 168*c* is expanded. An operator inserts the camera-side cable 12 into the slit 168*b* in this state, and fixes the camera-side cable with the hold mechanism. Thereafter, push-down of the cable holding portion 168*d* is canceled such that the pull spring 168*c* is shrunk, and thus the cable holding portion 168*d* is moved in the upward direction in the figure. Consequently, tensile force is applied to the camera-side cable 12, and thus the camera-side cable 12 is fixed in a stretched state.

The cable holder may be a cable holder obtained through a combination of the respective configurations described in the present embodiment. The cable holder may be provided with a component into which at least two of a cable holding portion, a push spring or a pull spring, and an air plug portion are integrated.

A slit of the cable holder may have a width at which the support member 13 can be inserted into the slit. Consequently, the cable holder may be used as a post-fitted support member operation member such as operation member 152 and operation member 153. With this configuration, the cable holder may be used as a holding member holding a position of the support member 13 between the support member 13 inserted into the trocar 31 and the trocar 31, or between the support member 13 directly inserted into an abdominal wall and the abdominal wall.

As mentioned above, tensile force is applied to the camera-side cable 12 by using the cable holder described in the present embodiment such that the camera-side cable 12 is fixed, and thus it is possible to prevent the camera-side cable 12 from becoming loose.

Embodiment 9

Still another embodiment of the present invention will be described as follows with reference to FIGS. 29 to 34. For convenience of description, a member having the same function as that of the member described in the embodiments will be given the same reference numeral, and description thereof will not be repeated.

Example 1 of Fixing Tool

Figure 29:
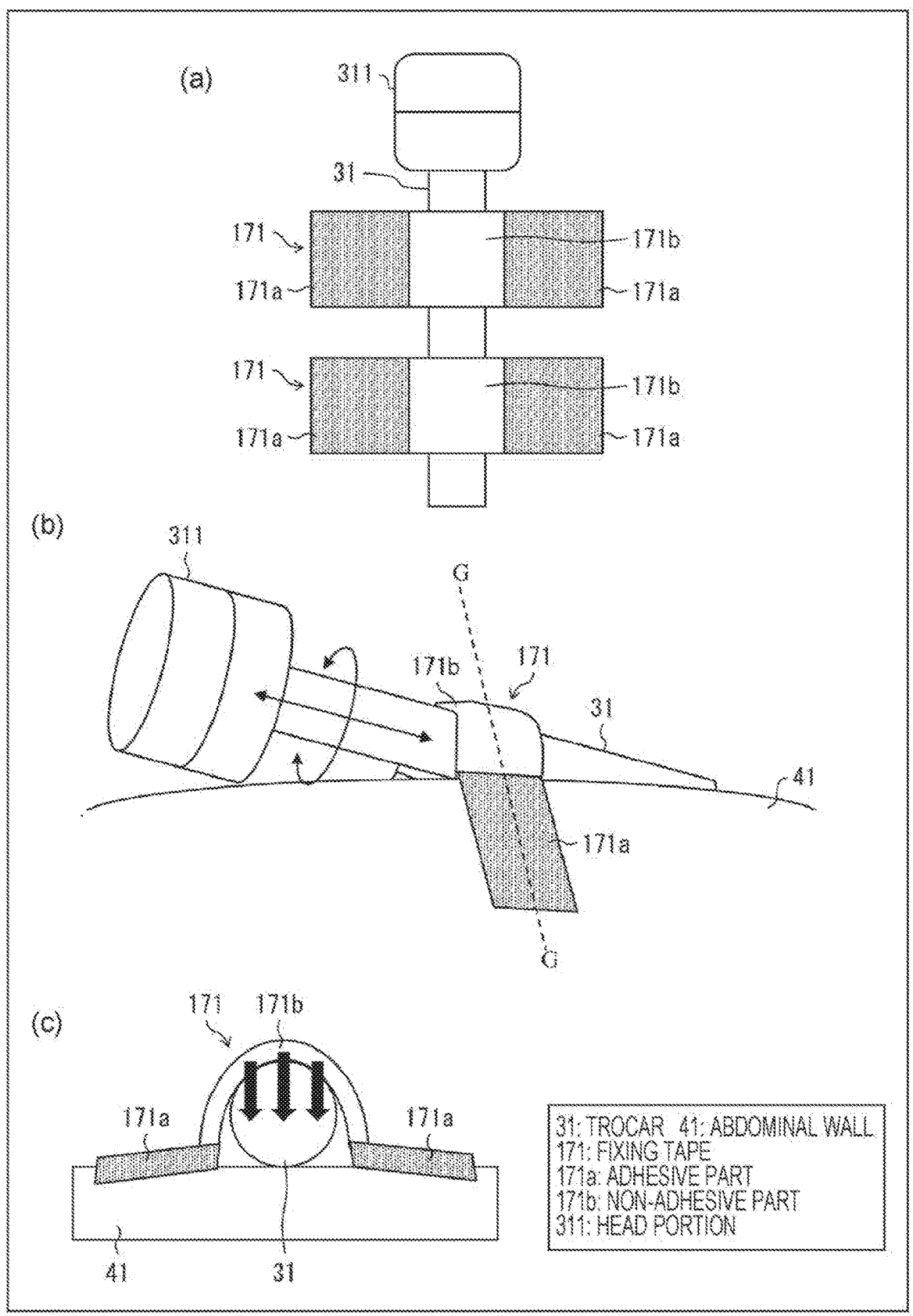
FIG. 29 illustrates still another embodiment of the present invention, and is a diagram illustrating an example of a fixing tool.

FIG. 29 is a diagram illustrating an example of a fixing tool according to the present embodiment. FIG. 29(a) is a top view illustrating the trocar 31 fixed to an abdominal wall via a fixing tape 171. FIG. 29(b) is a perspective view illustrating the trocar 31 fixed to the abdominal wall via the fixing tape 171. FIG. 29(c) is a sectional view taken along the line GG in FIG. 29(b). In other words, the fixing tool may be the fixing tape 171. As illustrated in FIG. 29(a), the fixing tape 171 has, at both ends, one surface serving as adhesive parts 171a having adhesiveness and a non-adhesive part 171b between the adhesive parts 171a.

An operator brings the non-adhesive part 171b of the fixing tape 171 into contact with the trocar 31 inserted into the abdominal wall, and sticks the adhesive part 171a to the abdominal wall while pulling the fixing tape 171 in the direction of the adhesive part 171a. Consequently, as illustrated in FIG. 29(c), pressing force is applied to the trocar 31 from the non-adhesive part 171b, and thus the trocar 31 is fixed onto the abdominal wall.

As described above, since the trocar 31 is brought into contact with the non-adhesive part 171b of the fixing tape 171, as illustrated in FIG. 29(b), an operator can rotate the trocar 31 in the outer circumferential direction, or insert and extract the trocar 31 into and out of the abdominal wall.

Example 2 of Fixing Tool

Figure 30:
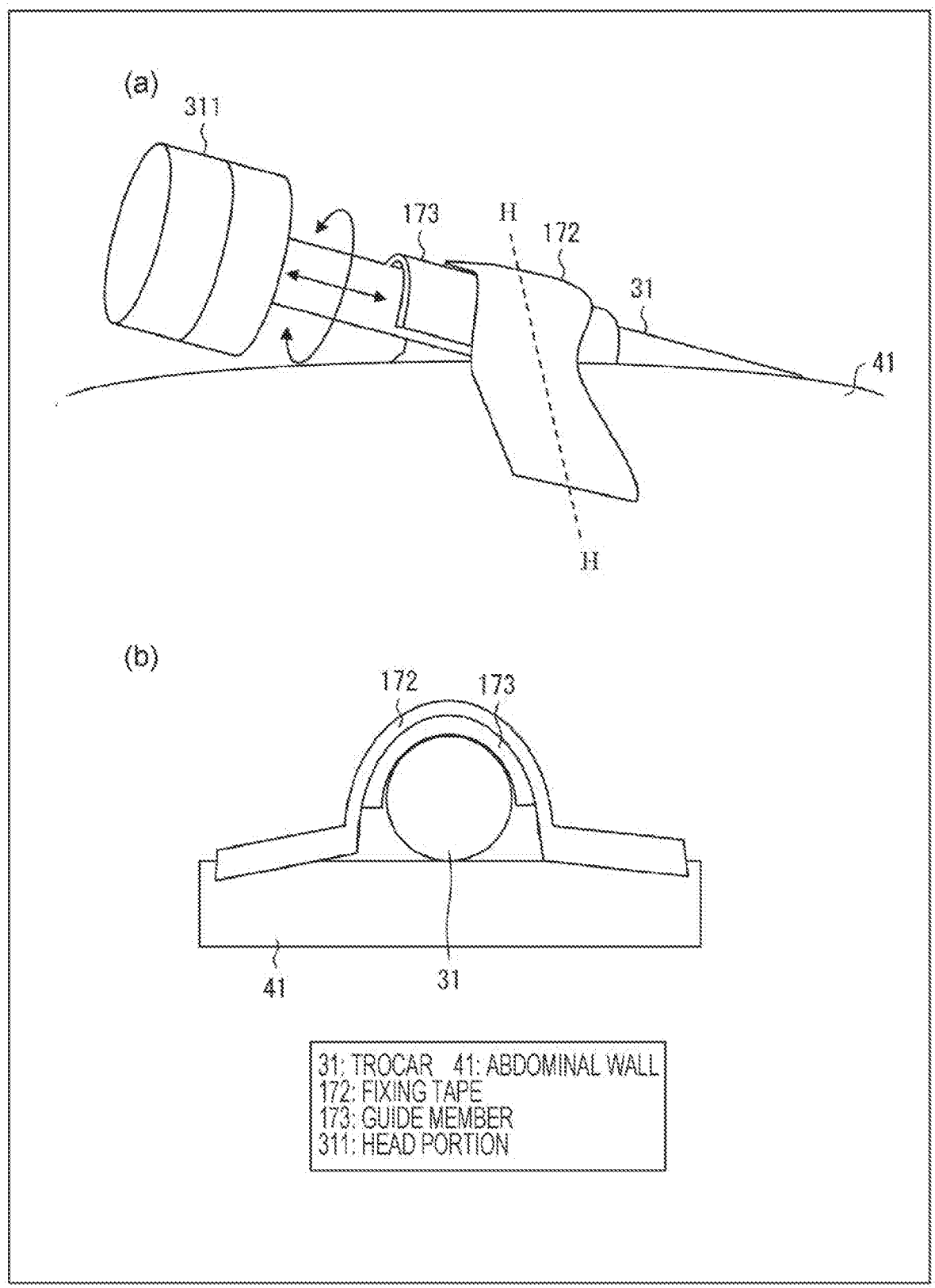
FIG. 30 is a diagram illustrating another example of the fixing tool.

FIG. 30 is a diagram illustrating another example of a fixing tool according to the present embodiment. In other words, the fixing tool may be a combination of a fixing tape 172 and a guide member 173 illustrated. The fixing tape 172 has one surface that entirely serves as an adhesive part with adhesiveness and in which there is no non-adhesive part. The guide member 173 is formed of a member that is hard to some extent and of which a surface is slidable, such as a resin.

FIG. 30(a) is a perspective view illustrating the guide member 173 and the trocar 31 fixed to the abdominal wall via the fixing tape 172, and FIG. 30(b) is a sectional view taken along the line HH in FIG. 30(a). An operator brings the guide member 173 into contact with the trocar 31 inserted into the abdominal wall, and sticks the trocar 31 to the abdominal wall for each guide member 173 while pulling the fixing tape 172 in the long side direction. Consequently, the trocar 31 is fixed onto the abdominal wall. The guide member 173 is used, and thus deviation of the trocar 31 can be reduced.

Example 3 of Fixing Tool

Figure 31:
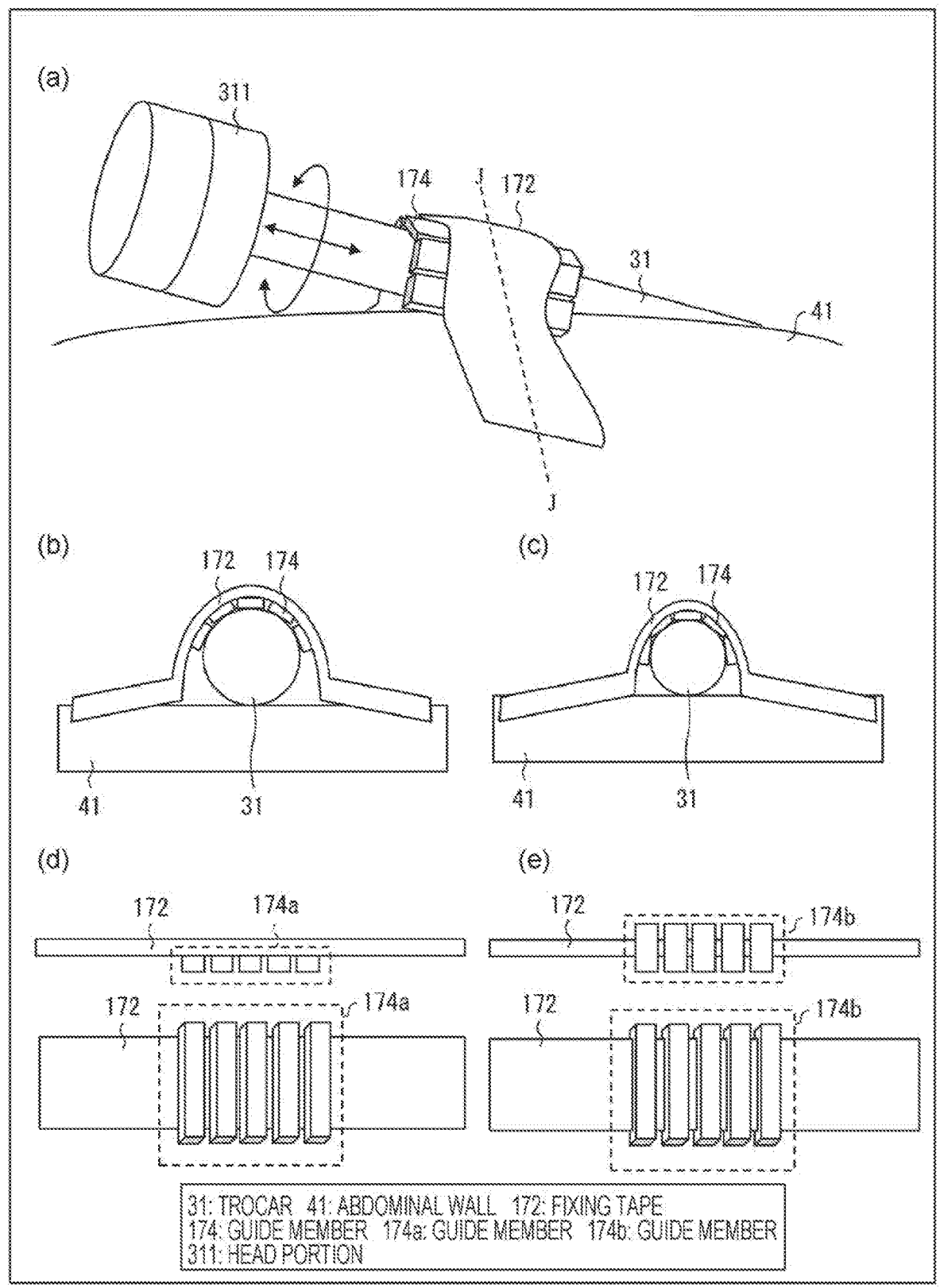
FIG. 31 is a diagram illustrating still another example of the fixing tool.

In a case of the fixing tool illustrated in FIG. 30, it is necessary to prepare a plurality of guide members 173 depending on a diameter of the trocar 31. In order to solve this problem, the fixing tool may include a guide member 174 illustrated in FIG. 31. FIG. 31 is a diagram illustrating still another example of a fixing tool according to the present embodiment.

FIG. 31(a) is a perspective view the guide member 174 and the trocar 31 fixed to the abdominal wall via the fixing tape 172. FIGS. 31(b) and 31(c) are sectional views taken along the line JJ in FIG. 31(a). FIGS. 31(d) and 31(e) are diagrams illustrating detailed configurations of the fixing tool.

As illustrated, the guide member 174 is a plurality of flat plates. In the fixing tool in this example, as illustrated in FIGS. 31(d) and 31(e), a plurality of flat plates are stuck to the fixing tape 172 with gaps, or the fixing tape 172 passes through a plurality of flat plates in which gaps are formed. In other words, in a guide member 174b illustrated in FIG. 31(e), each flat plate is provided with a hole through which the fixing tape 172 passes. On the other hand, in a guide member 174a illustrated in FIG. 31(d), each flat plate may or not be provided with a hole.

The guide member 174 is formed of a plurality of flat plates, and thus the fixing tool can be used regardless of diameters of the trocars 31 as illustrated in FIGS. 31(b) and 31(c).

Example 4 of Fixing Tool

Figure 32:
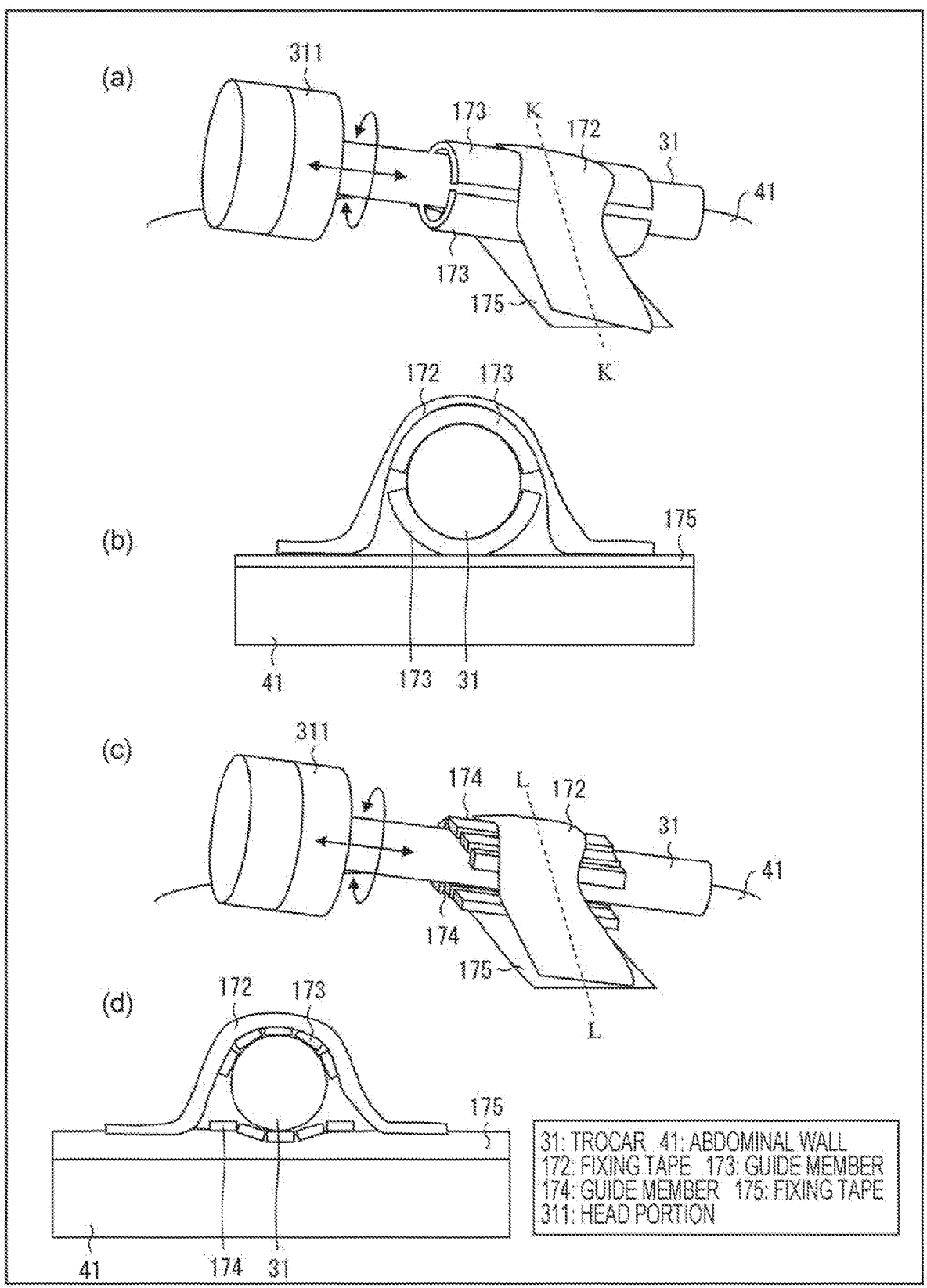
FIG. 32 is a diagram illustrating still another example of the fixing tool.

FIG. 32 is a diagram illustrating still another example of a fixing tool according to the present embodiment. FIG. 32(a) is a perspective view illustrating the guide members 173 and the trocar 31 fixed to the abdominal wall via the fixing tape 172. FIG. 32(b) is a sectional view taken along the line KK in FIG. 32(a). FIG. 32(c) is a perspective view illustrating the guide member 174 and the trocar 31. FIG. 32(d) is a sectional view taken along the line LL in FIG. 32(c).

In the examples illustrated in FIGS. 29 to 31, the trocar 31 is configured to be pressed against and fixed to the abdominal wall. In contrast, the guide member 173 described in FIG. 30 the guide member 174 described in FIG. 31 may be disposed between the abdominal wall and the trocar 31.

Specifically, an operator sticks one surface of a fixing tape 175 having both adhesive surfaces to the abdominal wall, and sticks the other surface thereof to the guide member 173 or the guide member 174. The trocar 31 is disposed in accordance with the guide member 173 or the guide member 174, and, as illustrated, the trocar 31 is interposed between the guide members 173 or the guide members 174. Finally, the guide member 173 or the guide member 174 is stuck to the fixing tape 175 (or the abdominal wall) while pulling the fixing tape 172 in the long side direction.

Particularly, the guide member 174 is used, the guide member 174 brought into contact with the abdominal wall is sunk on the abdominal wall along a shape of the trocar 31, and thus the trocar 31 can be more appropriately disposed.

Example 5 of Fixing Tool

Figure 33:
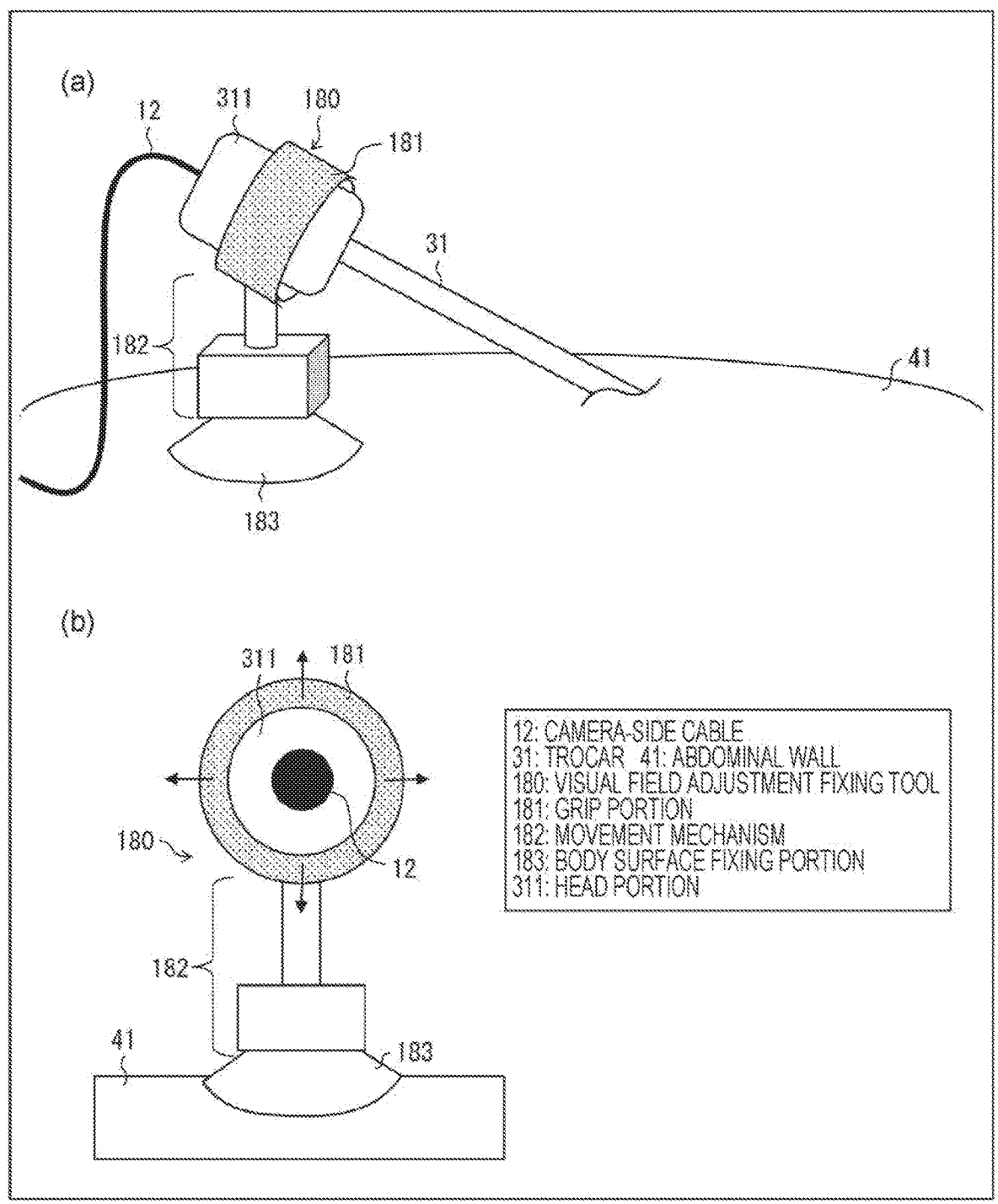
FIG. 33 is a diagram illustrating still another example of the fixing tool.

FIG. 33 is a diagram illustrating still another example of a fixing tool according to the present embodiment. The fixing tool of the illustrated example is a fixing tool causing the trocar 31 (in other words, the camera unit 11) to be moved more widely.

Specifically, as illustrated, a visual field adjustment fixing tool 180 is provided with a grip portion 181, a movement mechanism 182, and a body surface fixing portion 183. The grip portion 181 is a portion gripped by an operator. In the illustrated example, the visual field adjustment fixing tool is attached to a head portion 311 of the trocar 31, but an attachment location is not limited to the illustrated example. The movement mechanism 182 is a mechanism causing the grip portion 181 to be movable. The body surface fixing portion 183 is a portion fixing the visual field adjustment fixing tool 180 to the abdominal wall. In the illustrated example, the body surface fixing portion 183 is a sucker, but is not limited thereto. Details of configurations of the grip portion 181, the movement mechanism 182, and the body surface fixing portion 183 will be described later.

FIG. 33(b) is a sectional view illustrating the visual field adjustment fixing tool 180, the head portion 311 fixed by the visual field adjustment fixing tool 180, and the camera-side cable 12 passing through the head portion 311. Actually, the support member 13 is present between the head portion 311 and the camera-side cable 12, but is not illustrated in FIG. 33(b).

As illustrated, the grip portion 181 is movable in the upward-downward direction and the leftward-rightward direction in FIG. 33(b) by the movement mechanism 182. Consequently, an operator can widely move the trocar 31, and can thus widely move the camera unit 11 inside of the body. Therefore, the operator can widely change an imaging position.

Figure 34:
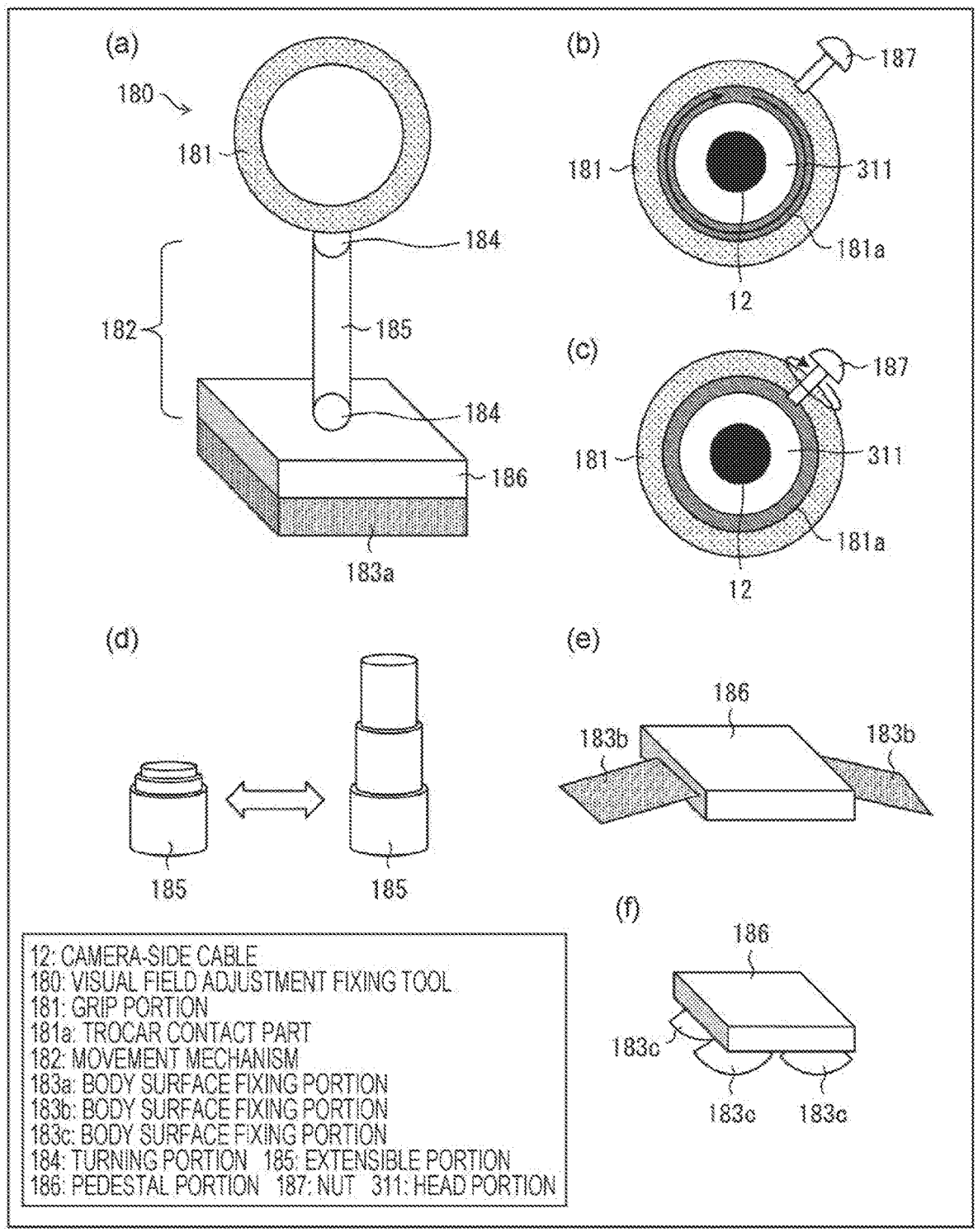
FIG. 34 is a diagram illustrating details of the fixing tool illustrated in FIG. 33.

FIG. 34 is a diagram illustrating details of each member of the visual field adjustment fixing tool 180. FIG. 34(a) is a diagram illustrating an example of the visual field adjustment fixing tool 180. As illustrated, the movement mechanism 182 is provided with turning portions 184, an extensible portion 185, and a pedestal portion 186. The pedestal portion 186 connects the body surface fixing portion 183 to the movement mechanism 182. The turning portions 184 are mechanisms causing the grip portion 181 to be turnable, and are, for example, spherical members provided at both ends of the extensible portion 185. The turning portions 184 are provided, and thus an operator can rotate or incline the grip portion 181. In other words, the operator can adjust a direction of the grip portion 181 by using the turning portions 184.

FIG. 34(d) is a diagram illustrating details of the extensible portion 185. As illustrated, the extensible portion 185 is configured to be extensible, and thus an inclination of the trocar 31 with respect to the abdominal wall can be changed. A configuration of the extensible portion 185 is not limited to the illustrated example as long as the extensible portion is extensible.

FIGS. 34(b) and 34(c) are diagrams illustrating details of the grip portion 181. In order to make gripping of the trocar 31 and rotation of the trocar 31 in the outer circumferential direction compatible, as illustrated, the grip portion 181 has a configuration in which only a trocar contact part 181a in contact with the trocar 31 (the head portion 311 in the illustrated example) is rotatable in the outer circumferential direction. On the other hand, it is also necessary to prevent rotation of the trocar 31 in the outer circumferential direction. Thus, the grip portion 181 is provided with a nut 187 as illustrated. As illustrated, the nut 187 is inserted into the grip portion, and thus the nut 187 can reach the trocar contact part 181a to stop rotation of the trocar contact part 181a. Instead of the nut 187, the grip portion 181 may be provided with a switch of which a front end reaches the trocar contact part 181a by pushing the switch. In other words, a mechanism for stopping rotation of the trocar contact part 181a is not particularly limited.

The trocar contact part 181a is required to be made of a material that is hard to some extent in order to be fixed with the nut 187 or the switch. On the other hand, the trocar contact part 181a is required to have some extent of flexibility in order to grip the trocars 31 with various shapes. Thus, the trocar contact part 181a is preferably made of a flexible material such as a balloon or a sponge.

In the illustrated example, a description has been made of an example in which a screw hole is formed in the columnar grip portion 181, but the grip portion 181 is not limited to this example. For example, the grip portion 181 may be a member in which a slit is formed over both ends and of which a section has a "C" shape.

Next, with reference to FIGS. 34(a), 34(e), and 34(f), details of the body surface fixing portion 183 will be described. FIGS. 34(e) and 34(f) are diagrams for describing variations of the body surface fixing portion 183.

Instead of the body surface fixing portion 183 that is a single sucker illustrated in FIG. 33, for example, a body surface fixing portion 183a, a body surface fixing portion 183b, and a body surface fixing portion 183c illustrated in FIGS. 34(a), 34(e), and 34(f) may be used. In the body surface fixing portion 183a illustrated in FIG. 34(a), at least a part brought into contact with the abdominal wall is an adhesive material that is adhesive. The body surface fixing portion 183b illustrated in FIG. 34(e) is a tape, and may be provided integrally with or separately from the pedestal portion 186. In the former case, a part of the body surface fixing portion 183b brought into contact with the abdominal wall may be adhesive. On the other hand, in the latter case, in the body surface fixing portion 183b, in addition to the part brought into contact with the abdominal wall, a part brought into contact with the pedestal portion 186 is required to be adhesive. The body surface fixing portion 183c illustrated in FIG. 34(f) is a plurality of suckers.

As mentioned above, the trocar 31 is fixed to the abdominal wall by using the fixing tools described in the present embodiment, and thus it is possible to prevent an unexpected change in an imaging direction due to vibration during an operation or collision with an operator's hand or an instrument. All of the fixing tools described in the present embodiment allow the trocar 31 to be inserted into or extracted from the abdominal wall or the trocar 31 to be rotated in the outer circumferential direction. Consequently, an operator can easily adjust a visual field direction of the camera unit 11. A direction of the camera unit 11 can also be changed by using the visual field adjustment fixing tool 180 illustrated in FIGS. 33 and 34.

SUMMARY

The in-vivo camera device 3 related to Aspect 1 of the present invention includes an imaging unit (camera unit 11)

that is introduced into a body; the support member 13 that has a connection portion (trocar connection portion 13*x*) with a tubular instrument (trocar 31) of which one end is introduced into the body at a front end side and has a joint portion with the imaging unit at a rear end side; and a cable (camera-side cable 12) that is connected to the imaging unit and passes through the support member 13, in which the connection portion is formed such that a front end side is formed thinner than a rear end side, the support member 13 is connected to the tubular instrument in a state in which the connection portion is fitted into the tubular instrument, and the support member 13 has a stabilization structure for stabilizing connection with the tubular instrument.

According to the configuration, connection between the tubular instrument and the support member is stabilized by the stabilization structure for stabilizing connection with the tubular instrument. Consequently, it is possible to provide an in-vivo camera device more excellent in usability.

According to the in-vivo camera device 3 related to Aspect 2 of the present invention, in Aspect 1, the support member 13 has the guide introduction portion 13*e* that is formed to be relatively longer at the front end side relative to the connection portion as the stabilization structure.

According to the configuration, even though the cable becomes loose, the long guide introduction portion provided on the front end side of the support member 13 is caught in the tubular instrument, and thus complete release of the support member 13 from the tubular instrument is less likely to occur. The complete release is avoided, and thus the cable can be easily returned to an original position by simply pulling the cable. Even though the cable becomes loose, and thus the support member 13 is inclined with respect to the tubular instrument, the long guide introduction portion is brought into contact with an inner wall of the tubular instrument such that an inclination of the support member 13 is restricted, and thus it is possible to reduce an angular deviation in a visual field direction. In other words, consequently, it is possible to stabilize connection between the support member 13 and the tubular instrument.

According to the in-vivo camera device 3 related to Aspect 3, in Aspect 2, the guide introduction portion 13*e* is formed such that a front end is thinner than a rear end.

According to the configuration, the front end of the guide introduction portion 13*e* is thinned, and thus introduction into the tubular instrument can be smoothly performed.

According to the in-vivo camera device 3 related to Aspect 4 of the present invention, in Aspects 2 or 3, an elastic body (elastic member 13*h*) is attached to a front end side of the guide introduction portion.

According to the configuration, in a case where the support member 13 is inclined with respect to the tubular instrument, the elastic body comes into contact with the inner wall of the tubular instrument earlier than the front end side of the guide introduction portion 13*e*. Therefore, inclination of the support member 13 can be more effectively suppressed, and thus an angular deviation in the visual field direction can be further reduced. Since friction force between the elastic body and the tubular instrument is large, release from the tubular instrument can be further made to be less likely to occur.

According to the in-vivo camera device 3 related to Aspect 5 of the present invention, in Aspect 1, the connection portion of the support member 13 is formed in a stepped shape that has a plurality of columnar parts (the small-diameter trocar connection part 13*x*-2 and the large-diameter trocar connection part 13*x*-1) being coaxial with each other and conforming to an inner diameter of the tubular instrument, as the stabilization structure.

According to the configuration, the connection portion is formed in a stepped shape having a plurality of columnar parts being coaxial with each other and conforming to an inner diameter of the tubular instrument, and can thus be connected to the tubular instrument by using a columnar part according to the inner diameter of the tubular instrument. Since a columnar shape is used, and thus contact with the inner wall of the tubular instrument is surface contact, it is possible to increase fixation strength between the tubular instrument and the support member. The fixation strength is increased, and thus release from the tubular instrument is less likely to occur. Since the contact with the inner wall of the tubular instrument is surface contact, it is possible to substantially reliably prevent the support member 13 from being inclined with respect to the tubular instrument. In other words, consequently, it is possible to stabilize connection between the support member 13 and the tubular instrument.

According to the in-vivo camera device 3 related to Aspect 6 of the present invention, in Aspect 5, the plurality of columnar parts is formed to be relatively long in an axial direction.

According to the configuration, an area of surface contact with the inner wall of the tubular instrument is increased by the columnar part that is formed to be relatively long in the axial direction, and thus it is possible to further increase fixation strength between the tubular instrument and the support member. The long columnar part can more relatively prevent the support member 13 from being inclined with respect to the tubular instrument.

According to the in-vivo camera device 3 related to Aspect 7 of the present invention, in Aspects 5 or 6, the columnar parts are formed of an elastic body.

According to the configuration, in addition to the effect of Aspects 5 or 6, it is possible to further increase fixation strength between the tubular instrument and the support member 13 due to elastic force (restoring force) of the elastic body and friction force of the contact surface.

According to the in-vivo camera device 3 related to Aspect 8 of the present invention, in Aspect 1, the connection portion of the support member has a plurality of columnar parts (the small-diameter trocar connection part 13*x*-2 and the large-diameter trocar connection part 13*x*-1) being coaxial with each other and conforming to an inner diameter of the tubular instrument, and the tapered parts 13*x*-3 and 13*x*-4 spreading from rear ends of the respective columnar parts, as the stabilization structure.

According to the configuration, the connection portion can be connected to the tubular instrument by using a columnar part conforming to the inner diameter of the tubular instrument. The tapered parts 13*x*-3 and 13*x*-4 spreading from the rear ends of the columnar parts function as stoppers butting with the end of the tubular instrument, and can thus receive and hold the tubular instrument even in a case where an inner diameter of the tubular instrument is slightly larger than the columnar part.

Consequently, contact with the inner wall of the tubular instrument is surface contact, it is possible to increase fixation strength between the tubular instrument and the support member. The fixation strength is increased, and thus release from the tubular instrument is less likely to occur. Since the contact with the inner wall of the tubular instrument is surface contact, it is possible to substantially reliably prevent the support member 13 from being inclined with respect to the tubular instrument. In other words, consequently, it is possible to stabilize connection between the support member 13 and the tubular instrument.

According to the in-vivo camera device 3 related to Aspect 9 of the present invention, in Aspect 8, the connection portion is formed of an elastic body.

According to the configuration, in addition to the effects of Aspect 8, it is possible to further increase fixation strength between the tubular instrument and the support member 13 due to elastic force (restoring force) of the elastic body and friction force of the contact surface.

According to the in-vivo camera device 3 related to Aspect 10 of the present invention, in Aspect 1, the connection portion of the support member is formed of an elastic body as the stabilization structure.

According to the configuration, the connection portion is formed of an elastic body, and thus the support member 13 and the inner wall of the tubular instrument is subjected to surface contact. Consequently, it is possible to increase fixation strength between the tubular instrument and the support member. In addition, it is possible to further increase fixation strength between the tubular instrument and the support member 13 due to elastic force (restoring force) of the elastic body and friction force of the contact surface. In other words, consequently, it is possible to stabilize connection between the support member 13 and the tubular instrument.

According to the in-vivo monitoring camera system 1 related to Aspect 11 of the present invention includes the in-vivo camera device according to any one of Aspects 1 to 10, and a control system including at least a display device.

According to the configuration, the control system includes the display device, and thus a captured image of the inside of the body can be displayed.

The present invention is not limited to each of the above-described embodiments, various changes may occur within the scope of the claims, and embodiments obtained through appropriate combination of the technical means described in the different embodiments are also included in the technical scope of the present invention. A novel technical feature may be obtained through combination of the technical means described in the respective embodiments.

REFERENCE SIGNS LIST

1 IN-VIVO MONITORING CAMERA SYSTEM
3 IN-VIVO CAMERA DEVICE
11 CAMERA UNIT
12 CAMERA-SIDE CABLE
13 SUPPORT MEMBER
13e GUIDE INTRODUCTION PORTION
13h ELASTIC MEMBER (ELASTIC BODY)
13x TROCAR CONNECTION PORTION
13x-1 LARGE-DIAMETER TROCAR CONNECTION PART (COLUMNAR PART)
13x-2 SMALL-DIAMETER TROCAR CONNECTION PART (COLUMNAR PART)
13x-3, 13x-4 TAPERED PART
13y PROTRUSION TYPE JOINT PORTION
13z ROOT PORTION
13z-1 COLUMNAR PART
14 DEPRESSION TYPE JOINT PORTION
15a CAMERA-SIDE CABLE CONNECTOR
15b APPARATUS-SIDE CABLE CONNECTOR
16 APPARATUS-SIDE CABLE
17 CAMERA UNIT CONTROL APPARATUS (CONTROL SYSTEM)
18 DISPLAY (DISPLAY DEVICE, CONTROL SYSTEM)
31 TROCAR (TUBULAR INSTRUMENT)
33, 33a, 33b, 33c FORCEPS
34 ENDOSCOPE
41 ABDOMINAL WALL

The invention claimed is:

1. An in-vivo camera device comprising:
an imaging unit that is introduced into a body;
a support member that has a connection portion connected to a tubular instrument at a front end side of the support member and has a joint portion connected to the imaging unit at a rear end side of the support member, wherein one end of the tubular instrument is introduced into the body; and
a cable that is connected to the imaging unit and passes through the support member wherein,
the connection portion is formed such that a front end side of the connection portion is formed thinner than a rear end side of the connection portion,
the support member is connected to the tubular instrument in a state in which the connection portion is fitted into the tubular instrument, and
the support member has a stabilization structure for stabilizing connection with the tubular instrument,
wherein the connection portion of the support member has a plurality of columnar parts being coaxial with each other and conforming to an inner diameter of the tubular instrument, and a plurality of tapered parts spreading from rear ends of the respective columnar parts, as the stabilization structure.

2. The in-vivo camera device according to claim 1, wherein the connection portion is formed of an elastic body.

3. An in-vivo monitoring camera system comprising:
the in-vivo camera device according to claim 1; and
a control system that includes at least a display device.

4. An in-vivo camera device comprising:
an imaging unit that is introduced into a body;
a support member that has a connection portion connected to a tubular instrument at a front end side of the support member and has a joint portion connected to the imaging unit at a rear end side of the support member, wherein one end of the tubular instrument is introduced into the body; and
a cable that is connected to the imaging unit and passes through the support member wherein,
the connection portion is formed such that a front end side of the connection portion is formed thinner than a rear end side of the connection portion,
the support member is connected to the tubular instrument in a state in which the connection portion is fitted into the tubular instrument, and
the support member has a stabilization structure for stabilizing connection with the tubular instrument,
wherein the connection portion of the support member is formed in a stepped shape that has a plurality of columnar parts being coaxial with each other and conforming to an inner diameter of the tubular instrument, as the stabilization structure.

5. The in-vivo camera device according to claim 4, wherein the plurality of columnar parts is formed to be longer in an axis direction than in a direction crossing the axis.

6. The in-vivo camera device according to claim 4, wherein the plurality of columnar parts is formed of an elastic body.

\* \* \* \* \*